United States Patent
Gooding et al.

(10) Patent No.: US 11,000,414 B2
(45) Date of Patent: May 11, 2021

(54) VACUUM LOSS DETECTION DURING LASER EYE SURGERY

(71) Applicant: AMO Development, LLC, Santa Ana, CA (US)

(72) Inventors: Phillip Gooding, Mountain View, CA (US); Christine Beltran, Sunnyvale, CA (US); Michael Campos, Fremont, CA (US); Jan Wysopal, Livermore, CA (US); Brent Eikanas, Brentwood, CA (US); Rene Hugues, Santa Clara, CA (US)

(73) Assignee: AMO Development, LLC, Santa Ana, CA (US)

( * ) Notice: Subject to any disclaimer, the term of this patent is extended or adjusted under 35 U.S.C. 154(b) by 70 days.

(21) Appl. No.: 16/409,731

(22) Filed: May 10, 2019

(65) Prior Publication Data
US 2019/0262174 A1    Aug. 29, 2019

Related U.S. Application Data

(60) Division of application No. 14/661,951, filed on Mar. 18, 2015, now Pat. No. 10,285,860, which is a
(Continued)

(51) Int. Cl.
| A61F 9/008 | (2006.01) |
| A61F 9/009 | (2006.01) |
| A61M 1/00 | (2006.01) |

(52) U.S. Cl.
CPC .............. *A61F 9/009* (2013.01); *A61F 9/008* (2013.01); *A61M 1/0052* (2014.02);
(Continued)

(58) Field of Classification Search
CPC .. A61M 2205/3344; A61M 2210/0612; A61M 1/0052; A61M 1/0025;
(Continued)

(56) References Cited

U.S. PATENT DOCUMENTS

| 5,116,203 A | 5/1992 | Natwick et al. |
| 5,459,570 A | 10/1995 | Swanson et al. |

(Continued)

FOREIGN PATENT DOCUMENTS

| WO | 2006090217 A1 | 8/2006 |
| WO | 2008157674 A1 | 12/2008 |
| WO | 2011163507 A2 | 12/2011 |

OTHER PUBLICATIONS

International Search Report and Written Opinion for Application No. PCT/US2015/065500, dated Mar. 31, 2016, 14 pages.

*Primary Examiner* — Rex R Holmes
(74) *Attorney, Agent, or Firm* — Johnson & Johnson Surgical Vision, Inc.

(57) ABSTRACT

Apparatus to treat an eye with an ophthalmic laser system comprises a patient interface having an annular retention structure to couple to an anterior surface of the eye. The retention structure is coupled to a suction line to couple the retention structure to the eye with suction. Liquid is added above the eye to act as a transmissive medium. A coupling sensor is coupled to the suction line to determine coupling of the retention structure to the eye. A separate pressure monitoring circuit having a much smaller volume than the suction line is connected to the annular retention structure to measure suction pressure therein. A system processor coupled to the monitoring pressure sensor includes instructions to interrupt firing of a laser when the pressure measured with a monitoring pressure sensor rises above a threshold amount.

10 Claims, 15 Drawing Sheets

Related U.S. Application Data continuation-in-part of application No. 14/068,994, filed on Oct. 31, 2013, now Pat. No. 9,987,165.

(60) Provisional application No. 61/721,693, filed on Nov. 2, 2012.

(52) U.S. Cl.
CPC ... *A61F 9/00825* (2013.01); *A61F 2009/0087* (2013.01); *A61F 2009/00851* (2013.01); *A61F 2009/00872* (2013.01); *A61M 1/005* (2014.02); *A61M 1/0025* (2014.02); *A61M 1/0031* (2013.01); *A61M 2205/3344* (2013.01); *A61M 2210/0612* (2013.01)

(58) Field of Classification Search
CPC ..... A61M 1/0031; A61M 1/005; A61F 9/009; A61F 9/008; A61F 2009/00851; A61F 2009/0087; A61F 2009/00872; A61F 9/00825

See application file for complete search history.

(56) References Cited

U.S. PATENT DOCUMENTS

| | | |
|---|---|---|
| 5,720,894 A | 2/1998 | Neev et al. |
| 5,748,352 A | 5/1998 | Hattori |
| 5,748,898 A | 5/1998 | Ueda |
| 5,957,915 A | 9/1999 | Trost |
| 5,984,916 A | 11/1999 | Lai |
| 6,019,472 A | 2/2000 | Koester et al. |
| 6,053,613 A | 4/2000 | Wei et al. |
| 6,111,645 A | 8/2000 | Tearney et al. |
| 6,254,590 B1 | 7/2001 | Vaillancourt |
| 6,454,761 B1 | 9/2002 | Freedman |
| 7,655,002 B2 | 2/2010 | Myers, I et al. |
| 7,717,907 B2 | 5/2010 | Ruiz et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 2005/0192562 A1* | 9/2005 | Loesel .................. A61F 9/009 606/5 |
| 2007/0209425 A1 | 9/2007 | Shibata et al. |
| 2009/0118663 A1 | 5/2009 | Rockley et al. |
| 2010/0042059 A1* | 2/2010 | Pratt .................. A61M 1/0049 604/318 |
| 2010/0234835 A1 | 9/2010 | Horikawa et al. |
| 2010/0274228 A1* | 10/2010 | Mrochen ................ A61F 9/013 604/541 |
| 2011/0190739 A1 | 8/2011 | Frey et al. |
| 2011/0319873 A1* | 12/2011 | Raksi ..................... A61F 9/009 606/1 |
| 2011/0319875 A1 | 12/2011 | Loesel et al. |
| 2013/0056082 A1 | 3/2013 | Nunez et al. |
| 2013/0291593 A1 | 11/2013 | Roh et al. |
| 2014/0128821 A1 | 5/2014 | Gooding et al. |
| 2015/0190278 A1 | 7/2015 | Gooding et al. |

\* cited by examiner

400

- 405- Provide fluid collector having a volume with a porous structure
- 410- Provide suction line
- 415- Place patient on support
- 420- Place speculum in eye
- 425- Place retention structure with suction ring on eye to define container
- 430- Align eye with retention structure
- 435- Apply coupling suction to eye
- 440- Measure eye coupling suction upstream of porous structure
- 445- Measure suction down stream of porous structure
- 450- Indicate when eye structure is held to eye with suction based on measured coupling suction
- 455- Apply liquid or viscous solution to container on eye
- 460- Indentify at least partial blockage of porous structure when coupling suction above a threshold and down stream suction below a second threshold
- 465- Repeat above steps until eye is coupled to retention structure
- 470- Couple docking structure to retention structure with axial movement
- 475- Apply suction to gap between retention structure and docking structure to clamp retention structure to docking structure with suction
- 480- Measure eye coupling suction
- 485- Determine alignment of eye with retention structure
- 490- Treat eye with laser
- 495- Measure eye coupling suction
- 500- Provide warning to user when eye coupling suction rises above a warning threshold
- 505- Interrupt laser firing when eye coupling suction above an interruption threshold pressure
- 510- Provide indicator to user when coupling pressure above the threshold pressure
- 515- Re-align eye with retention structure
- 520- Re-couple eye to retention structure
- 525- Resume laser treatment
- 530- Finish laser treatment
- 535- Decouple eye from retention structure
- 540- Decouple retention structure from docking structure
- 545- Complete remaining portion of the surgery

*FIG. 17*

VACUUM LOSS DETECTION DURING LASER EYE SURGERY

CROSS-REFERENCE TO RELATED APPLICATIONS

This application is a divisional of and claims priority to U.S. patent application Ser. No. 14/661,951, filed Mar. 18, 2015, which is a continuation-in-part of U.S. patent application Ser. No. 14/068,994, filed Oct. 31, 2013, now U.S. Pat. No. 9,987,165, which claims the benefit of priority to U.S. Provisional Application No. 61/721,693, filed Nov. 2, 2012, the entire contents of which are hereby incorporated by reference in their entirety for all purposes as if fully set forth herein.

FIELD OF THE INVENTION

The present disclosure relates generally to surgery. Although specific reference is made to tissue retention for laser eye surgery, embodiments as described herein can be used in one or more of many ways with many surgical procedures and devices, such as orthopedic surgery, robotic surgery and microkeratomes.

BACKGROUND OF THE INVENTION

Cutting of materials can be done mechanically with chisels, knives, scalpels and other tools such as surgical tools. However, prior methods and apparatus of cutting can be less than desirable and provide less than ideal results in at least some instances. For example, at least some prior methods and apparatus for cutting materials such as tissue may provide a somewhat rougher surface than would be ideal. Although lasers having pulse short pulse durations have been proposed to cut tissue, these short pulsed lasers may use very high pulse repetition rates and the energy of these lasers can be difficult to measure in at least some instances. Pulsed lasers can be used to cut one or more of many materials and have been used for laser surgery to cut tissue.

Examples of surgically tissue cutting include cutting the cornea and crystalline lens of the eye. The lens of the eye can be cut to correct a defect of the lens, for example to remove a cataract, and the tissues of the eye can be cut to access the lens. For example the cornea can be cut to access the cataractous lens. The cornea can be cut in order to correct a refractive error of the eye, for example with laser assisted in situ keratomileusis (hereinafter "LASIK").

Many patients may have visual errors associated with the refractive properties of the eye such as nearsightedness, farsightedness and astigmatism. Astigmatism may occur when the corneal curvature is unequal in two or more directions. Nearsightedness can occur when light focuses before the retina, and farsightedness can occur with light refracted to a focus behind the retina. There are numerous prior surgical approaches for reshaping the cornea, including laser assisted in situ keratomileusis, all laser LASIK, femto LASIK, corneaplasty, astigmatic keratotomy, corneal relaxing incision (hereinafter "CRT"), and Limbal Relaxing Incision (hereinafter "LRI"). Astigmatic Keratotomy, Corneal Relaxing Incision (CRT), and Limbal Relaxing Incision (LRI), corneal incisions are made in a well-defined manner and depth to allow the cornea to change shape to become more spherical.

Cataract extraction is a frequently performed surgical procedure. A cataract is formed by opacification of the crystalline lens of the eye. The cataract scatters light passing through the lens and may perceptibly degrade vision. A cataract can vary in degree from slight to complete opacity. Early in the development of an age-related cataract the power of the lens may increase, causing near-sightedness (myopia). Gradual yellowing and opacification of the lens may reduce the perception of blue colors as those shorter wavelengths are more strongly absorbed and scattered within the cataractous crystalline lens. Cataract formation may often progresses slowly resulting in progressive vision loss.

A cataract treatment may involve replacing the opaque crystalline lens with an artificial intraocular lens (IOL), and an estimated 15 million cataract surgeries per year are performed worldwide. Cataract surgery can be performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small round hole can be formed in the anterior side of the lens capsule. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye.

Although prior methods and apparatus have been proposed to cut tissue, the fixation of tissue of these prior methods and apparatus can be less than ideal in at least some respects. For example, the prior microkeratomes that have been used to cut corneal tissue with blades can result in less than ideal fixation of the eye, and may provide incomplete or inaccurate cutting of the tissue in at least some instances. Also, at least some of the prior microkeratomes may result in temporary increases in intraocular pressure (hereinafter "TOP") in at least some instances. Although prior laser systems have been proposed to cut tissue with short laser beam pulses, the methods and apparatus to couple the laser beam to the eye can be less than ideal in at least some instance. For example, at least some of the prior system can result in one or more of increased TOP, incomplete coupling to the eye, or patient movement relative to the laser in at least some instances. Although many patients have been successfully treated with the prior systems, the less than ideal coupling to the patient can result in a somewhat irregular treatment, or an incomplete treatment, for example. Work in relation to embodiments suggests that the coupling of the eye to the laser may be related to variability in the flow of suction to the eye. Also, the feedback provided to the physician can be less than ideal in at least some instances. The less than ideal coupling of the laser to the patient may result in patient movement, or the patient decoupling from the laser system, or both, such that the cutting of tissue may be less than ideal.

Laser based cataract surgery relies on a patient interface device to stabilize the eye to assure proper laser treatment. These interface devices are typically attached to the eye with some type of annular "suction ring" design where a vacuum is applied. If there is a loss of vacuum during laser treatment it is important to shut off delivery of the laser energy before any mistreatment, or even injury, can occur. In most systems the vacuum level is monitored in the instrument at the end of the vacuum supply tube, so that the laser energy is shut off when the vacuum level at that point in the pneumatic circuit drops below a certain level, indicating the patient interface is not in complete suction contact with the eye. This level of monitoring may not react quickly enough in certain cases, in particular where fluid is present as an optical medium from the laser to the cornea.

Thus, improved methods and apparatus to couple patients to treatment devices such as lasers would be helpful.

SUMMARY

The improved methods and apparatus for retention of an eye as described herein can be used to provide safe and effective retention for surgery such as laser eye surgery. The retention structure may comprise an annular structure to couple to an anterior surface of the eye, such as one or more of the cornea, the limbus, or the conjunctiva. The annular structure can be coupled to a suction line so as to couple the annular structure to the eye with suction. In many embodiments, a coupling sensor is coupled to one or more of the annular structure or the suction line to determine coupling of the retention structure to the eye, such that coupling of the retention structure to the eye can be measured quickly. The determination of coupling of the retention structure to the eye can be provided to the surgeon so that the surgeon can take appropriate action, and may allow the laser treatment to be paused or interrupted. A fluid collecting container can be coupled to the annular structure to receive and collect liquid or viscous material from the container. A fluid stop comprising a float valve or a porous structure can be coupled to an outlet of the fluid collecting container so as to inhibit passage of the liquid or viscous material when the container has received an amount of the liquid or viscous material greater than a volume of a patient interface container on the eye. The fluid stop can inhibit the passage of liquid or viscous material to structures downstream of the fluid stop such as a pressure regulator and vacuum pump, so as to provide consistent gas flow. The coupling sensor can be coupled upstream of the porous structure to provide a rapid measurement of the coupling of the retention structure to the eye, and may be coupled upstream of the fluid collecting container to further improve the response time of the coupling sensor. The liquid or viscous material may comprise a viscosity and a density greater than a gas such as air, and the liquid or viscous material may comprise one or more of a solvent, water, a liquid material, a solution, saline, a viscous material, or a viscoelastic material. The porous structure may comprise one or more of a filter, a membrane, a porous membrane having holes, a plate having holes, a hydrophobic material or a porous material.

In a first aspect, embodiments provide an apparatus to treat an eye. The apparatus comprises a patient interface. The patient interface comprises an annular structure to engage an anterior surface of the eye. The annular structure comprises an opening to receive a portion of the eye and channel to couple to the eye with suction, and an optically transmissive structure to transmit light through the opening of the annular structure. The optically transmissive structure and the annular structure define portions of an interface container when coupled to the eye, and the interface container comprises an interface container volume. A fluid collection container comprises an inlet and an outlet. The inlet is coupled to the channel of the annular structure, and the fluid collection container comprises a collection volume greater than the interface container volume. A porous structure has channels sized to pass gas and inhibit flow of a liquid or viscous material received from the fluid collection container.

In another aspect, embodiments provide a method of treating an eye. The method comprises coupling a patient interface to the eye with suction so as to define an optically transmissive interface container on the eye. The interface container has an interface container volume comprising one or more of a liquid or a viscous material. One or more of the liquid or viscous material is received from the patient interface into a fluid collection container. Flow of the liquid or viscous material is inhibited with a porous structure when the fluid collection container has received an amount of the liquid or viscous material greater than the chamber volume.

In another aspect, embodiments provide an apparatus to treat an eye. The apparatus comprises an annular structure to engage an anterior surface of the eye. The annular structure comprises an opening to receive a portion of the eye and a channel to couple to the eye with suction. A porous structure is coupled to the annular structure with a suction line, and has channels sized to pass gas and inhibit flow of a liquid or viscous material from the container. A coupling sensor is coupled to one or more of the annular structure or the suction line upstream of the porous structure to determine coupling of the annular structure to the eye.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 17 shows a method of treating a patient with the eye retention apparatus.

DETAILED DESCRIPTION

Methods and systems related to laser eye surgery are disclosed. In many embodiments, a laser is used to form precise incisions in the cornea, in the lens capsule, and/or in the crystalline lens nucleus. Although specific reference is made to tissue retention for laser eye surgery, embodiments as described herein can be used in one or more of many ways with many surgical procedures and devices, such as orthopedic surgery, robotic surgery and microkeratomes.

The embodiments as describe herein are particularly well suited for treating tissue, such as with the surgical treatment of tissue. In many embodiments, the tissue comprises an optically transmissive tissue, such as tissue of an eye. The embodiments as described herein can be combined in many ways with one or more of many known surgical procedures such as cataract surgery, laser assisted in situ keratomileusis (hereinafter "LASIK"), laser assisted subepithelial keratectomy (hereinafter "LASEK").

Methods and systems related to laser treatment of materials and which can be used with eye surgery such as laser eye surgery are disclosed. A laser may be used to form precise incisions in the cornea, in the lens capsule, and/or in the crystalline lens nucleus, for example. The embodiments as described herein can be particularly well suited for coupling a retention structure to an eye so that movement of the eye can be decreased substantially, for example.

As used herein, the terms anterior and posterior refers to known orientations with respect to the patient. Depending on the orientation of the patient for surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

As used herein, the terms first and second are used to describe structures and methods without limitation as to the order of the structures and methods which can be in any order, as will be apparent to a person of ordinary skill in the art based on the teachings provided herein.

System Configuration

Figure 1:
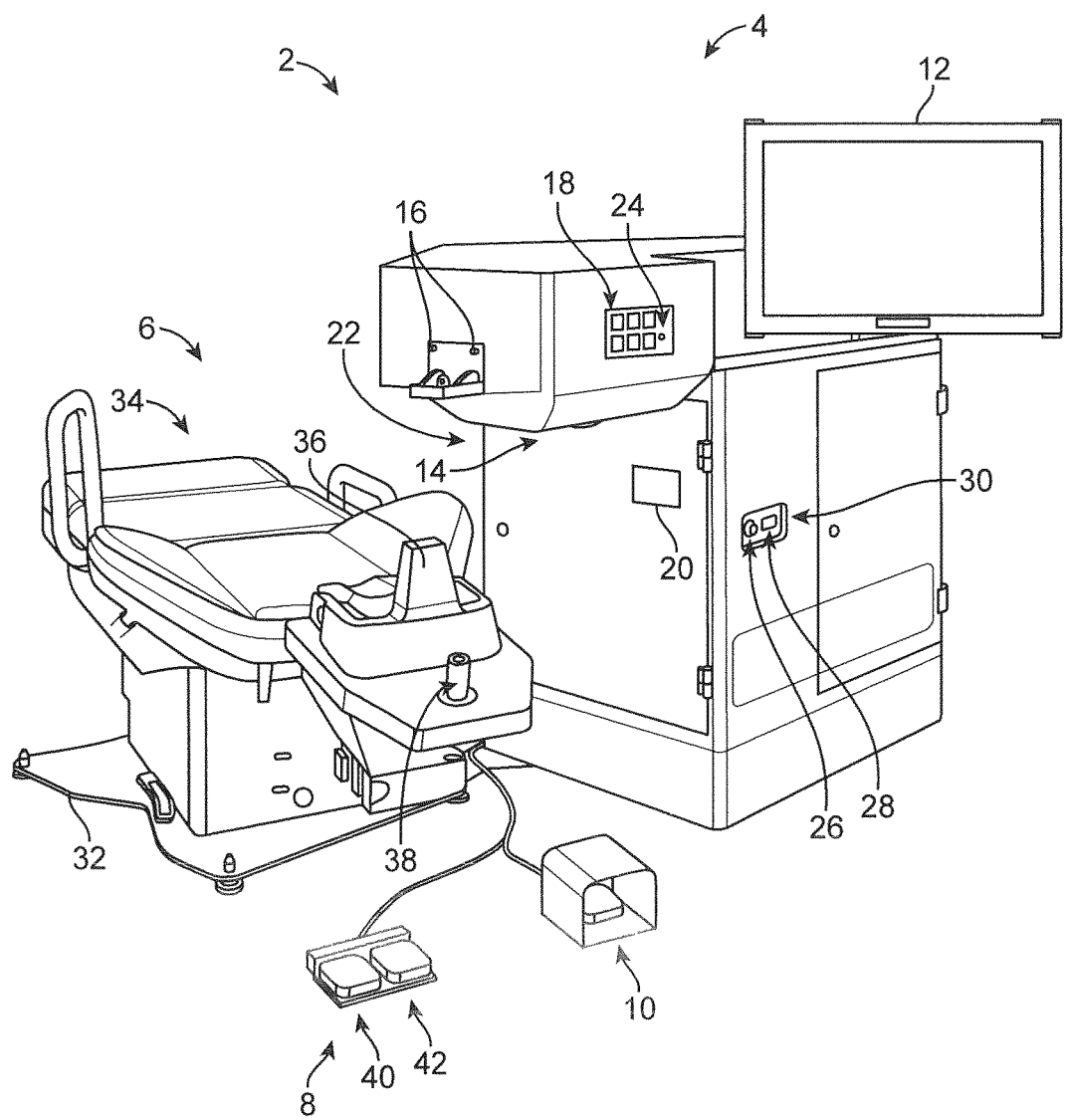
FIG. 1 shows a perspective view showing a laser eye surgery system.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support chair or bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38. To further protect against unintended chair motion, power supplied to the patient chair 6 may automatically be cut off using a switch.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user is without access to network based printing.

Figure 2:
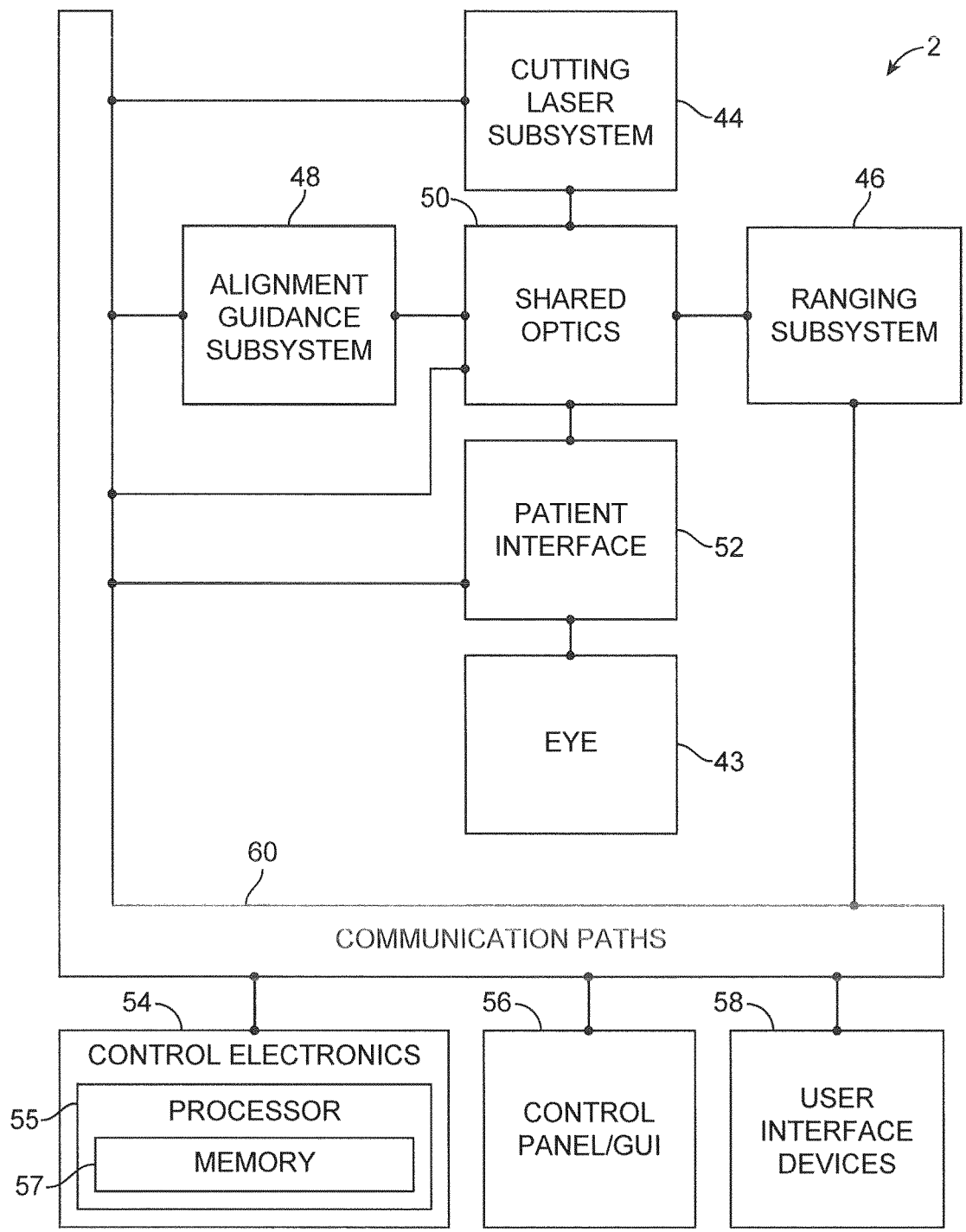
FIG. 2 shows a simplified block diagram showing a top level view of the configuration of a laser eye surgery system.

FIG. 2 shows a simplified block diagram of the system 2 coupled with a patient eye 43. The patient eye 43 comprises a cornea, a lens, and an iris. The iris defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately 10.sup.-13 seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, the ranging subsystem 46, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components.

The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The control electronics 54 may comprise a processor/controller 55 (referred to herein as a processor) that is used to perform calculations related to system operation and provide control signals to the various system elements. A computer readable medium 57 (also referred to as a database or a memory) is coupled to the processor 55 in order to store data used by the processor and other system elements. The processor 55 interacts with the other components of the system as described more fully throughout the present specification. In an embodiment, the memory 57 can include a look up table that can be utilized to control one or more components of the laser system as described herein.

The processor 55 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof, and the like.

The memory 57 can be local or distributed as appropriate to the particular application. Memory 57 may include a number of memories including a main random access memory (RAM) for storage of instructions and data during program execution and a read only memory (ROM) in which fixed instructions are stored. Thus, memory 57 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3:
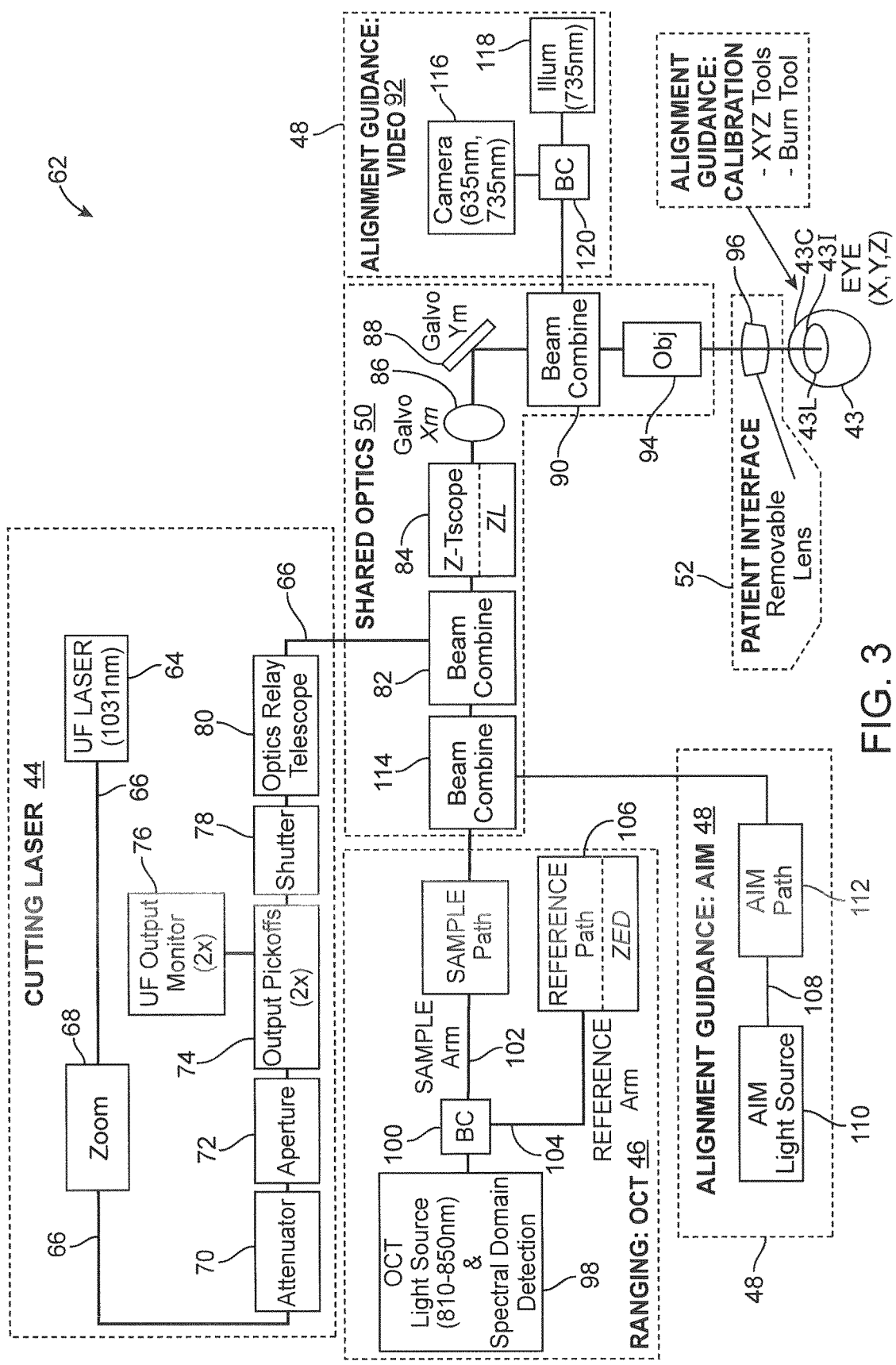
FIG. 3 shows is a simplified block diagram illustrating the configuration of an optical assembly of a laser eye surgery system.

FIG. 3 is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to be between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the xy galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2.times. beam expansion ratio and close to a 1:1 relationship of the movement of the lens group to the movement of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as z-scan device for scanning the focus point of the laser-pulse beam 66 in the patient's eye 43. The Z-telescope 84 can be controlled automatically and dynamically by the control electronics 54 and selected to be independent or to interplay with the X and Y scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 86 and the Y-Scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials placed on the docking structures and optical structures of the disposable lens such as the location of the anterior and posterior surfaces.

In the embodiment of FIG. 3, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others. Additionally the ranging subsystem such as an OCT can be used to detect features or aspects involved with the patient interface. Features can include fiducials placed on the docking structures and optical structures of the disposable lens such as the location of the anterior and posterior surfaces.

The ranging subsystem 46 in FIG. 3 includes an OCT light source and detection device 98. The OCT light source and detection device 98 includes a light source that generates and emits an OCT source beam with a suitable broad spectrum. For example, in many embodiments, the OCT light source and detection device 98 generates and emits the OCT source beam with a broad spectrum from 810 nm to 850 nm wavelength. The generated and emitted light is coupled to the device 98 by a single mode fiber optic connection.

The OCT source beam emitted from the OCT light source and detection device 98 is passed through a pickoff/combiner assembly 100, which divides the OCT source beam into a sample beam 102 and a reference portion 104. A significant portion of the sample beam 102 is transmitted through the shared optics 50. A relative small portion of the sample beam is reflected from the patient interface 52 and/or the patient's eye 43 and travels back through the shared optics 50, back through the pickoff/combiner assembly 100 and into the OCT light source and detection device 98. The reference portion 104 is transmitted along a reference path 106 having an adjustable path length. The reference path 106 is configured to receive the reference portion 104 from the pickoff/combiner assembly 100, propagate the reference portion 104 over an adjustable path length, and then return the reference portion 106 back to the pickoff/combiner assembly 100, which then directs the returned reference portion 104 back to the OCT light source and detection device 98. The OCT light source and detection device 98 then directs the returning small portion of the sample beam 102 and the returning reference portion 104 into a detection assembly, which employs a time domain detection technique, a frequency detection technique, or a single point detection technique. For example, a frequency domain technique can be used with an OCT wavelength of 830 nm and bandwidth of 100 nm.

Once combined with the UF laser pulse beam 66 subsequent to the beam combiner 82, the OCT sample beam 102 follows a shared path with the UF laser pulse beam 66 through the shared optics 50 and the patient interface 52. In this way, the OCT sample beam 102 is generally indicative of the location of the UF laser pulse beam 66. Similar to the UF laser beam, the OCT sample beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the pickoff/combiner assembly 100, and back into the OCT light source and detection device 98. The returning back reflections of the sample beam 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for an axially stationary surface in the eye of patient interface volume because the optical path length does not change as a function of different settings of the Z-telescope 84. The ranging subsystem 46 has an inherent Z range that is related to the light source and detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path via a stage ZED, 106 within ranging subsystem 46. Passing the OCT sample beam 102 through the Z-telescope 84, while not impacting the sample path length, allows for optimization of the OCT signal strength. This is accomplished by focusing the OCT sample beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample beam 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc, are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber, and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-field configuration such that the illumination sources are directed to the independent surfaces outside the capture numerical aperture of the image portion of the video system. Alternatively the illumination may also be in a bright field configuration. In both the dark and bright field configurations, the illumination light source maybe be used as a fixation beam for the patient. The illumination may also be used to illuminate the patients pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 52. The illumination light reflected and scattered off of various structures of the eye 43 and patient interface travel back through the patient interface 52, back through the objective lens assembly 94, and back to the beam combiner 90. At the beam combiner 90, the returning light is directed back to the beam combiner 120 where the returning light is redirected toward the camera 116. The beam combiner can be a cube, plate, or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be an suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 4:
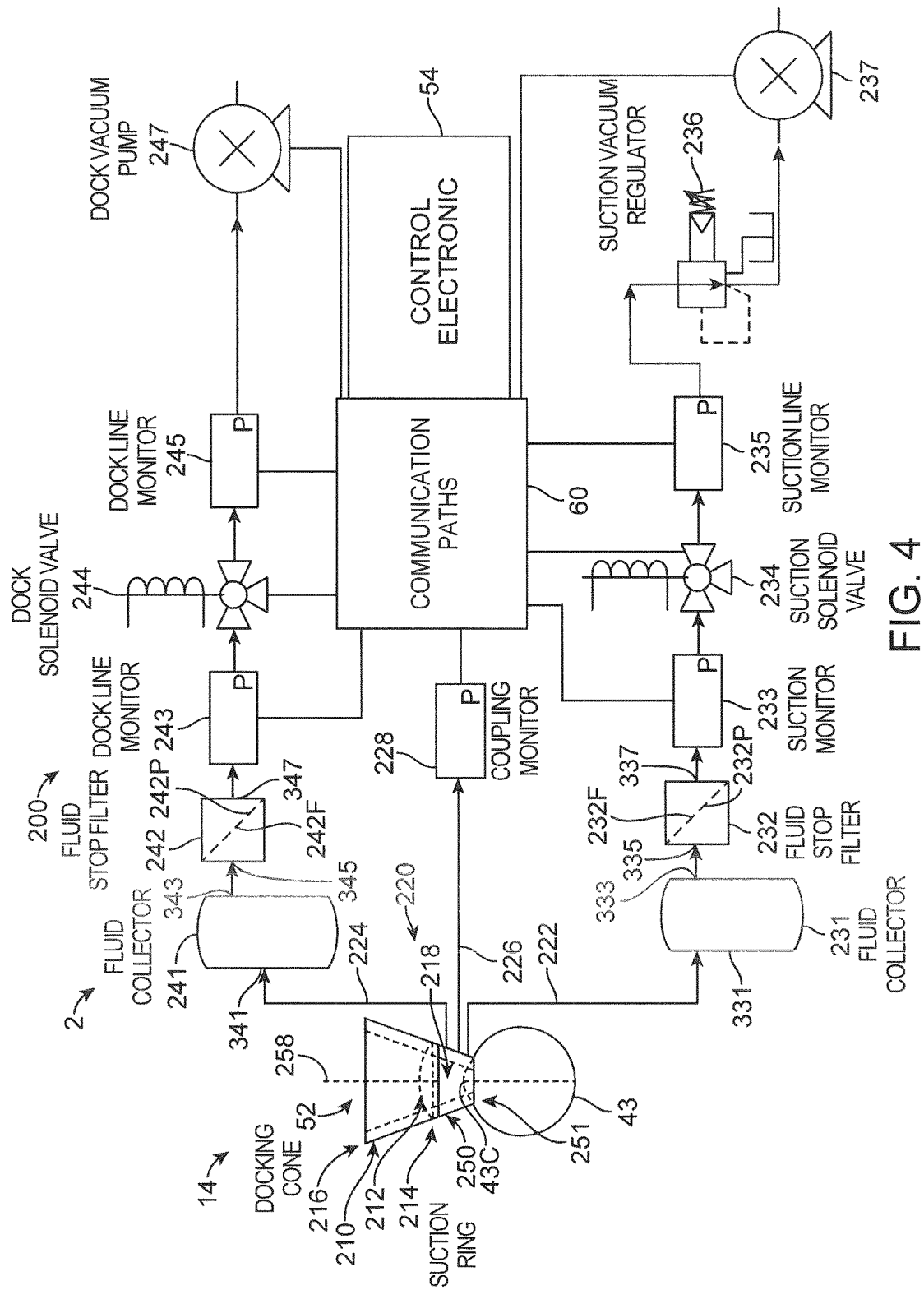
FIG. 4 shows a schematic diagram of the eye retention apparatus.

FIG. 4 shows a schematic diagram of an apparatus 200 to treat eye 43 comprising components of laser system 2 and patient interface assembly 52 as described herein. The patient interface assembly 52 may comprise a docking structure 210 and an eye retention structure 250. The docking structure 210 may comprise a docking cone and the eye retention structure 250 may comprise a suction ring. The patient interface assembly comprises an axis 258 substantially aligned with an axis of the laser system 2 and an axis of the eye 43. The axis 258 extends through an inner channel of docking structure 210 and an inner channel of the eye retention structure 250, and the axis 258 can be substantially concentric with respect to both of these structures. The eye retention structure 250 and the docking structure 210 may comprise components of the patient interface assembly, and these structures may be separable so as to define separate components of the patient interface assembly 52. Alternatively, the eye retention structure 250 and the docking structure 210 can be provided together as a substantially inseparable component of the patient interface assembly 52.

The docking structure 210 may comprise an anterior end portion 216 to couple to a receptacle of laser system 2, and a posterior end portion 214 to couple to the eye retention structure 250. The docking structure 210 may comprise a conical structure extending between anterior end portion 216 and posterior end portion 214. The docking structure 210 may comprise an optically transmissive structure 212 comprising an optically transmissive material and may comprise one or more of a first curved surface, a second curved surface, a first flat surface, a second flat surface, and a lens, a plate, or a wedge. The optically transmissive structure 214 may comprise lens 96, for example.

The optically transmissive structure 212 can be located on the docking structure 210 or the eye retention structure 250, or combinations thereof, for example. The posterior surface of the optically transmissive structure 210 and the inner surface of the eye retention structure substantially define an interface fluid container 218 when placed on the eye. The interface fluid container 218 comprises an interface fluid container volume.

The eye retention structure 250 comprises a posterior end portion having an opening 251 sized to receive at least a portion of the cornea 43C of eye 43. The eye retention structure 250 is coupled to one or more suction lines 220 to retain the eye 43 when the cornea 43C extends into opening 251. The one or more suction lines 220 may comprise a plurality of suction lines. The plurality of suction lines 220 may comprise first suction line 222 and second suction line 224.

The first suction line 222 extends from a suction ring of eye retention structure 250 to a vacuum source such as an eye retention structure vacuum pump 237. A plurality of components is coupled to suction line 222, and may be coupled along first suction line 222 in series. A first fluid collector comprising a first container 231 is coupled to eye retention structure 250 to receive fluid from eye retention structure 250. Line 222 may comprise tubing extending at least partially between eye retention structure 250 and first fluid collector comprising container 231, for example. The first fluid collector comprising first container 231 may comprise any one or more of many structures suitable to collect a liquid or viscous material as described herein, and the first fluid collector 231 may comprise a catchment, for example. Container 231 comprises an inlet 331 and an outlet 333. Container 231 comprises a container volume approximately corresponding to an amount of liquid stored in container 231 when a liquid is drawn into container 231 through inlet 331 with suction of outlet 333. A first fluid stop 232 is coupled to outlet 333 of first container 231. The first fluid stop 232 comprises a float valve 232F or a porous structure 232P to pass a gas such as air and inhibit flow of a liquid or viscous material as described herein, so as to stop substantially the flow of the liquid or viscous. The first fluid stop 232 comprises an inlet 335 and an outlet 337. The inlet 335 is coupled to the outlet 333 of the container 231. The outlet 337 of the fluid stop 232 is coupled to a suction monitor 233, which can be positioned along first suction line 222 in order to monitor suction of the line. In many embodiments, suction monitor 233 comprising the pressure sensor is positioned along the suction line downstream of the porous structure 232P and in many embodiments placed along the suction line 222 between the fluid stop 232 and a solenoid valve 234. The pressure sensor can be coupled to control electronics 54 with communication paths 60, as described herein. The pressure sensor may comprise one or more of many transducers responsive to pressure of suction line 222, and such transducers are known to a person of ordinary skill in the art. The suction solenoid valve 234 can be coupled to control electronics 54 with communication paths as described herein. The first suction line 222 may comprise a suction line monitor 235 to monitor suction downstream of suction solenoid valve 234. The suction line monitor 235 can be coupled to the first suction line 222 between suction solenoid valve 234 and a suction vacuum regulator 236. The suction vacuum regulator 236 can be provided along first suction line 222 so as to provide a regulated amount of pressure to eye 43 with the suction ring, for example suction pressure between about 300 and 500 mm Hg (millimeters Mercury), for example. The outlet of the suction vacuum regulator 236 is coupled to an inlet of the eye retention structure vacuum pump 237. The eye retention vacuum pump 237 may be coupled to control electronics 54 with communication paths 60.

The components along first suction line 222 can be configured in one or more of many ways to couple eye retention structure 250 to eye 43. In many embodiments, the first container 231 comprises a volume that is greater than a volume of container 218 of patient interface. When used to couple to the eye, retention structure 250 can be placed on eye 43 with the liquid or viscous material within container 218, and suction applied to retention structure 250. When the retention structure 250 is not sufficiently coupled to eye 43, the fluid of container 218 can be drawn into container 231 with suction. When a sufficient amount of the liquid or viscous material has been drawn into container 231, a portion of the liquid or viscous material is passed through outlet 333 and onto porous structure 232P so as to inhibit flow of fluid through the porous structure. Where the first fluid stop 232 comprises the float valve 232F, a portion of the liquid or viscous material is passed through outlet 333 and triggers the float valve 232F to close so as to inhibit flow of fluid through the first fluid stop 232. Alternatively, the fluid stop function of the porous structure 232P or the float valve 232F may be integrated into the fluid collector 241. The volume of the container 231 greater than the volume of container 218 allows the physician to place substantial amounts of fluid within container 218 when coupling the retention structure 250 to the eye. In many embodiments, the volume of container 218 comprises at least about twice the volume of the container 231, so that the user of system 2 has at least about two attempts to couple retention structure 250 to eye 43 before the flow of suction 222 is substantially inhibited by fluid stop 232. In many embodiments, the container 218 comprises a volume of about 0.5 to 2 cubic centimeters (hereinafter "cc") and container 231 comprises a volume within a range from about 1 to about 4 cc, for example.

In many embodiments, the ratio of container 231 to the ratio of container 218 can be limited such that the suction of line 222 can engage eye 2 with sufficient suction pressure in a sufficiently short amount of time, so that the retention structure can be readily used by a physician. In many embodiments, the volume of container 231 comprises no more than about twenty times the volume of container 218, for example no more than about five times the volume of container 218.

A coupling sensor 228 can be coupled to eye retention structure 250 in one or more of many ways, for example with a line 226 in order to monitor coupling of retention structure 250 to eye 43. Coupling sensor 228 may comprise one or more of a force transducer, or a pressure transducer, for example. In many embodiments, line 226 is fluidically coupled to a posterior annular suction ring of retention structure 250 upstream of fluid stop 232 such that coupling sensor 228 can rapidly measure changes in suction pressure and issue a warning to the user or interrupt the laser, for example, when an amount of pressure of line 226 rises above a threshold amount. Line 226 may comprise tubing, for example. Line 226 can be coupled upstream of fluid stop 232 in many ways can be directly coupled to retention structure 250 or coupled to line 222 upstream of fluid stop 232 so as to monitor coupling of retention structure 250 to eye 43. Coupling of line 226 upstream of fluid trap 232 can provide a more rapid response to changes in suction pressure than suction monitor 233 located downstream of fluid stop 232. The coupling sensor 228 can be coupled to electronic control 54 with communication paths 60 and the output of coupling sensor 228 can be used to control operation of laser system 2 as described herein.

The fluid stop 232 comprising porous structure 232P can be configured in one or more of many ways to inhibit flow of fluid along line 222 when container 231 has received a sufficient amount of the liquid or viscous material. The liquid or viscous material may comprise one or more of water, a liquid material, a solution, saline, a viscous material, or a viscoelastic material, for example. The liquid or viscous material may comprise a viscosity and density substantially greater than a gas such as air, and may be substantially incompressible, such that passage of the liquid or viscous material through the porous structure is substantially inhibited. The porous structure may comprise one or more of a filter, a membrane, a porous membrane having holes, a plate having holes or a hydrophobic material. The porous structure comprises channels, for example holes, sized so as to inhibit passage of the liquid or viscous material through the porous structure. The porous structure may comprise a membrane having holes formed in a hydrophobic material, the holes having a cross-sectional size of no more than about 10 um across so as to block the passage of the liquid or viscous material through the porous structure, for example.

The second suction line 224 extends from retention structure 250 to a vacuum source such as dock vacuum pump 247. The second suction line 224 can provide suction to an interface between docking structure 210 and eye retention structure 250, so as to suction clamp the docking structure 210 to the eye retention structure 250 when the patient is treated, for example. Line 224 may comprise tubing extending at least partially between eye retention structure 250 and second fluid collector comprising second container 241, for example. Dock vacuum pump 247 is coupled to an anterior portion of eye retention structure 250 so as to engage the anterior portion of the eye retention structure with docking structure 210, for example a docking cone. A second plurality of components is coupled to second suction line 224, and may be coupled along second suction line 224 in series. A second fluid collector comprising a second container 241 is coupled to eye retention structure 250 to receive fluid the anterior portion of eye retention structure 250 used to connect to docking structure 210. The second fluid collector comprising second container 241 may comprise any one or more of many structures suitable to collect a liquid or viscous material as described herein, and the second fluid collector 241 may comprise a catchment, for example. Second container 241 comprises an inlet 341 and an outlet 343. Second container 241 comprises a container volume approximately corresponding to an amount of liquid stored in container 241 when a liquid is drawn into container 241 through inlet 341 with suction of outlet 343. A second fluid stop 242 is coupled to outlet 343 of second container 241. The second fluid stop 242 comprises a second porous structure 242P or a second float valve 242F to pass a gas such as air an inhibit flow of a liquid or viscous material as described herein, so as to stop substantially the flow of the liquid or viscous. The second fluid stop 242 comprises an inlet 345 and an outlet 347. The inlet 345 is coupled to the outlet 343 of the second container 241. The outlet 347 of the second fluid stop 242 is coupled to a dock monitor 243, which can be positioned along second suction line 224 in order to monitor suction for coupling docking structure 210 to retention structure 250 as described herein. In many embodiments, suction monitor 243 comprising the pressure sensor is positioned along the second suction line downstream of the second porous structure 242P or second float valve 242F and in many embodiments placed along the second suction line 224 between the fluid second stop 242 and a second solenoid vale 244. The pressure sensor can be coupled to control electronics 54 with communication paths 60, as described herein. The pressure sensor may comprise one or more of many transducers responsive to pressure of suction line 224, and such transducers are known to a person of ordinary skill in the art. The suction solenoid valve 244 can be coupled to control electronics 54 with communication paths as described herein. The second suction line 224 may comprise a suction line monitor 245 to monitor suction downstream of suction solenoid valve 244. The suction line monitor 245 can be couple to an inlet of the vacuum pump 247. The vacuum pump 247 may be coupled to control electronics 54 with communication paths 60.

The second fluid collector comprising container 241 may comprise a volume less than first container 231, for example. The second fluid collector may collect substantially less fluid than the first fluid collector, as the first line 222 may often couple to retention structure 250 at a location below second line 224, for example. Decreasing the volume of the second container 241 may provide more rapid suction clamping of the docking structure 210 to the retention structure 250. Alternatively, the container 241 may comprise a volume that is greater than container 231, for example.

The coupling lines as described herein may comprise lines for fluidic coupling known to a person of ordinary skill in the art and may comprise one or more of tubing, flexible tubing, rigid tubing, plastic tubing, metal tubing or manifolds, for example. The containers as described herein may comprise similar materials and can be constructed by a person of ordinary skill in the art based on the teachings provided herein.

Figure 5:
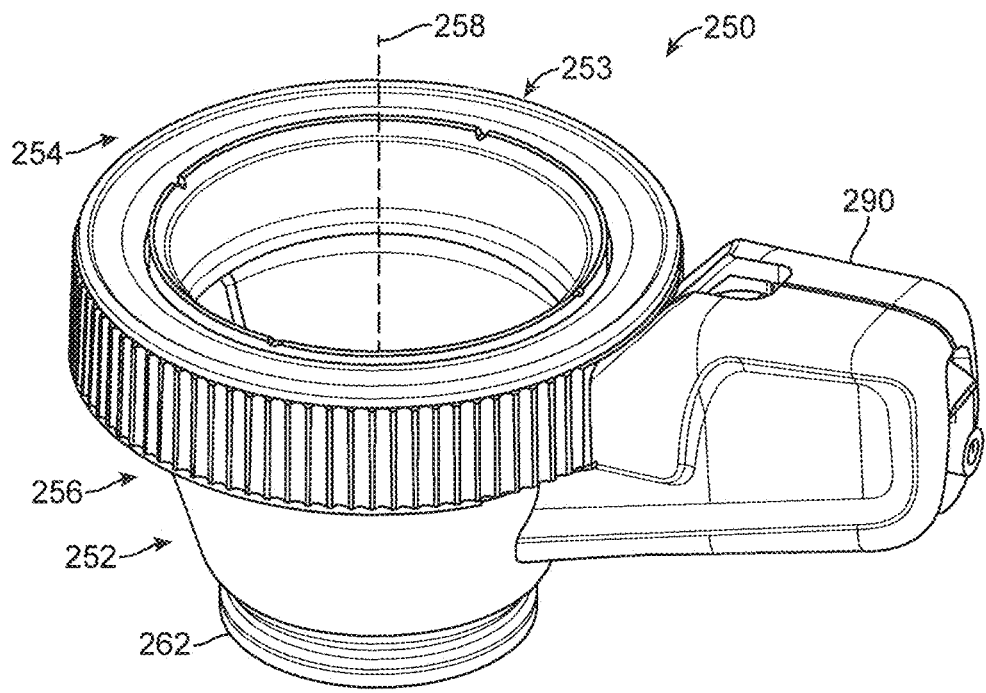
FIGS. 5 and 6 show a perspective view and a cross sectional view, respectively, of an eye retention structure.
Figure 6:
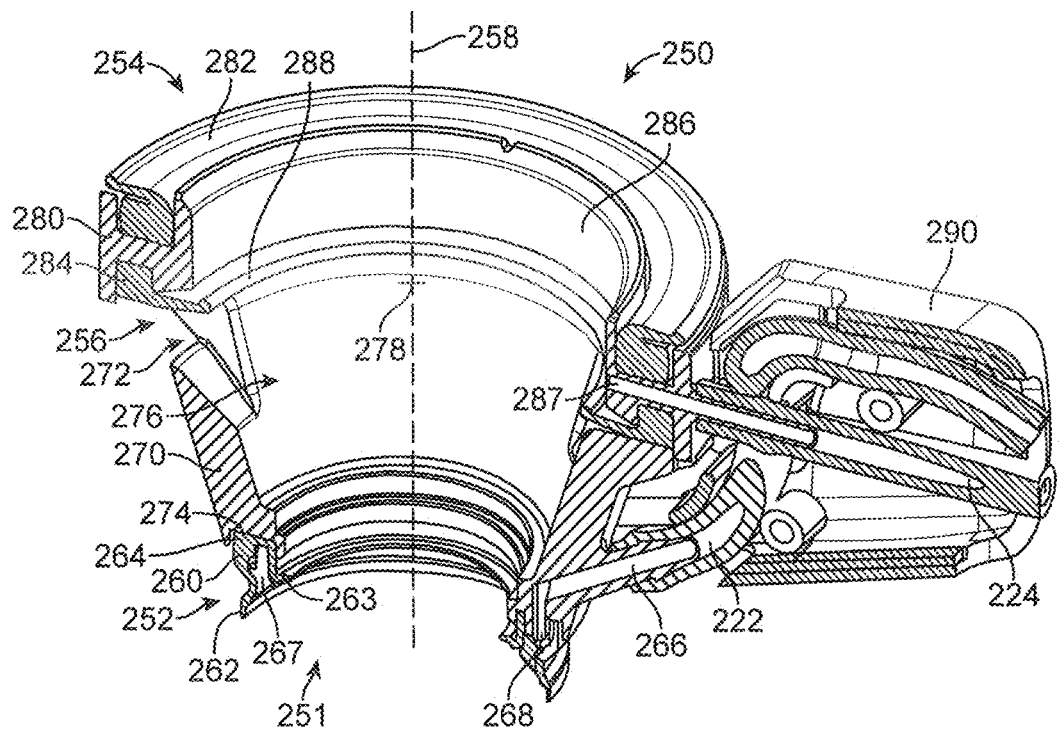

FIGS. 5 and 6 show a perspective view and a cross sectional view, respectively, of eye retention structure 250. Eye retention structure 250 comprises opening 251 on a posterior end portion 252 dimensioned to receive the cornea 43C of eye 43. The posterior end portion 252 may comprise an elastic suction ring 260. The eye retention structure 250 may comprise an anterior end portion 254 and an intermediate portion 256 extending between the posterior end portion 252 and the anterior end portion 254. The posterior end portion 252, the anterior end portion 254, and the intermediate section 256 can be located about an axis 258 for alignment with an axis of the eye, and for alignment with an optical axis of system 2, so as to align optical axis of system 2 with the eye 43. The eye retention structure 250 may comprise a handle 290. The first suction line 222 can be coupled to the interior of suction ring 260 with a channel 266 and an annular channel 268 extending substantially around an anterior portion of suction ring 260 interior.

The suction ring 260 may comprise an elastomeric component comprising medical grade silicon, for example. The suction ring 260 may comprise an outer rim 262 and an inner rim 263. The inner rim 263 and the outer rim 262 can be dimensioned so as to fit on a peripheral portion of cornea 43C and may engage a portion of the conjunctiva of the eye over the sclera of the eye, for example. The inner and outer rim can be located at different locations along axis 258 such that outer rim 262 comprise a posterior end of eye retention structure 250, and inner rime 263 is located anterior to the outer rim. The angle extending between outer rim 262 and inner rim 263 may correspond to an angle of the eye, so as to engage the eye and fix the eye with suction ring 260. The inner rim 263 and outer rim 262 may comprise sealing blades to form a seal with the eye and vacuum clamp to eye 43. The suction ring 260 may comprise a support bolster 267 to inhibit tissue movement between the inner rim 263 and the outer rim 262 upon application of suction.

The intermediate section 256 may comprise a stiff housing 270 to couple the eye to the docking structure 210. A channel 272 can be formed in housing 270 to allow placement of fluid into the chamber 218 and release of fluid from chamber 218 so as to inhibit pressure increases when container 218 is formed with the anterior surface of the eye. The housing 270 may comprise an annular channel 274 formed in a posterior surface of the housing to receive the annular suction ring 260. The housing 270 may comprise a passage defined with an inner surface 276. The inner surface of housing 270 may comprise a conical surface, such as a frustum of a cone for example. The docking structure 210 comprising the optically transmissive structure 212 can position a posterior surface of the optically transmissive structure 212 at location 278 along the axis 258. The volume of container 218 can be determined based on the dimensions of inner surface 278, the position of posterior surface of structure 212 along axis 258 and the approximate location of the cornea 43C along axis 258. The approximate location of cornea 43C along axis 258 may comprise correspond to the location of channel 274 which receives the suction ring. A substantial portion of container 218 can be define with stiff housing 270 such that container 218 comprises a substantially constant volume. The housing 270 can be rigid and may comprise a rigid material to add stiffness to the housing, for example a suitable plastic material.

The anterior end portion 254 may comprise an annular structure 280. The annular structure 280 may comprise an annular groove to receive a gasket 282 to engaging the docking structure 210. The annular structure 280 may extend substantially around anterior end portion 254 and comprise a portion of housing 270. The annular structure 280 may comprise an opening 287 to couple to second line 224 as described herein. The annular structure 280 may comprise an inner annular surface 286 dimensioned so as to guide the docking structure 210 toward an annular seal 284. The annular gasket 284 may comprise an inner rim 288 to contact the docking structure 210 and form a seal. The gasket 282 spaced apart from gasket 284, such that suction of second line 224 forms a vacuum clamp.

Figure 7:
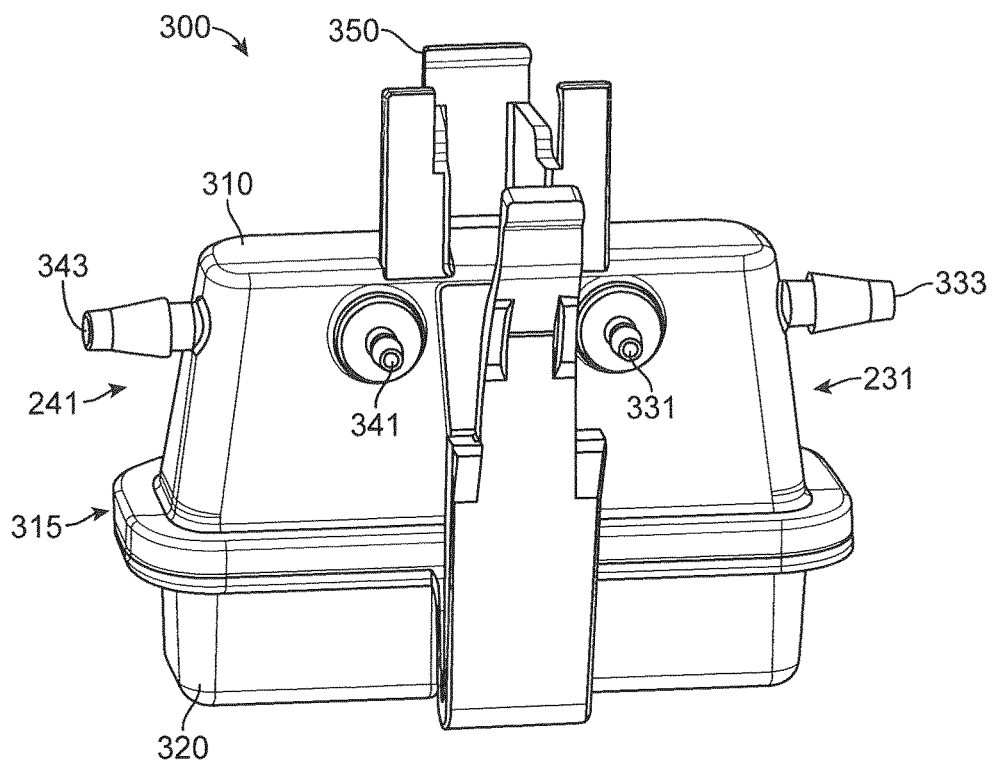
FIGS. 7 and 8 show perspective view of a container assembly to collect fluid received from the retention ring structure.
Figure 8:
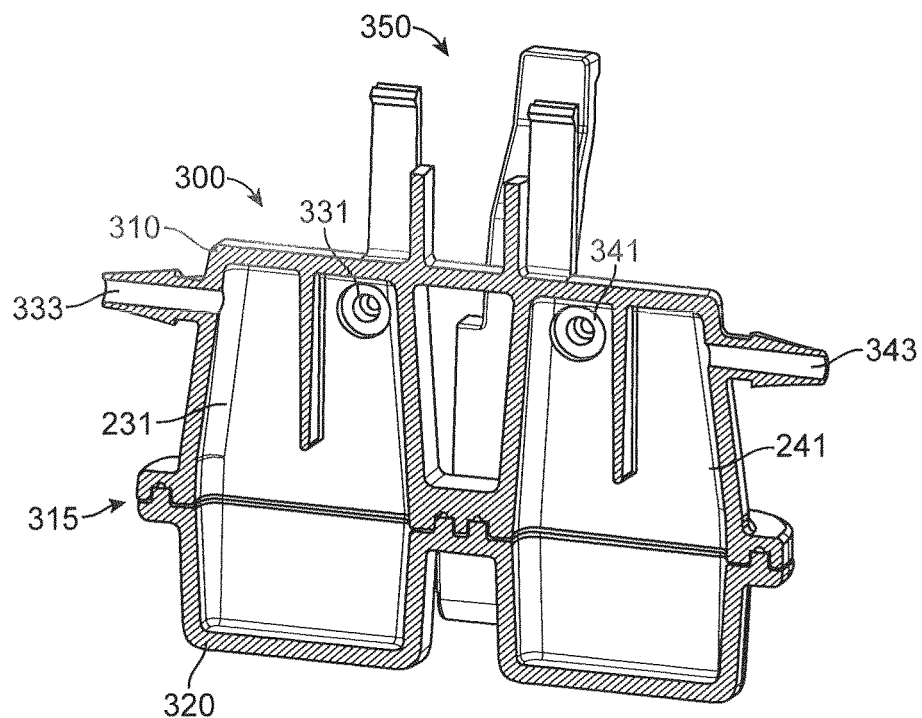

FIGS. 7 and 8 show perspective view of a container assembly 300 comprising a plurality of containers to collect material received from the retention ring structure. The plurality of containers may comprise first container 231 and second container 241. The first container 231 comprises inlet 331 and outlet 333, and the second container 241 comprises inlet 341 and outlet 343. The container assembly 300 comprises a mount 350 to hang the container assembly at a suitable location of system 2. The container assembly 300 comprises an anterior portion 310 and a posterior portion 320. The anterior portion may be joined to the posterior portion with a joint 315 extending there between. The joint 315 may comprise one or more of a snap fitting, a compression fitting, a friction fitting, ultrasonic weld, or an adhesive, for example.

Figure 9A:
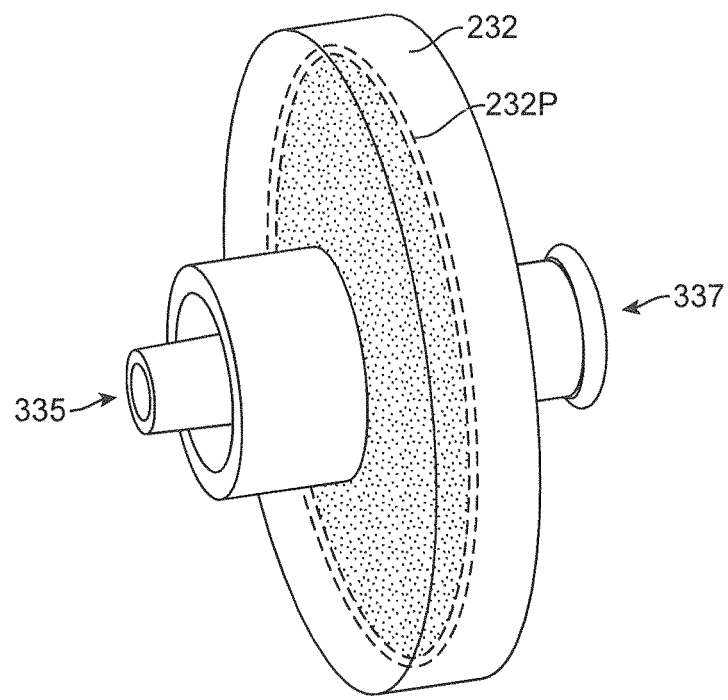
FIGS. 9A and 9B show a fluid inhibiting structure comprising a porous structure to inhibit flow of a liquid or viscous material.
Figure 9B:
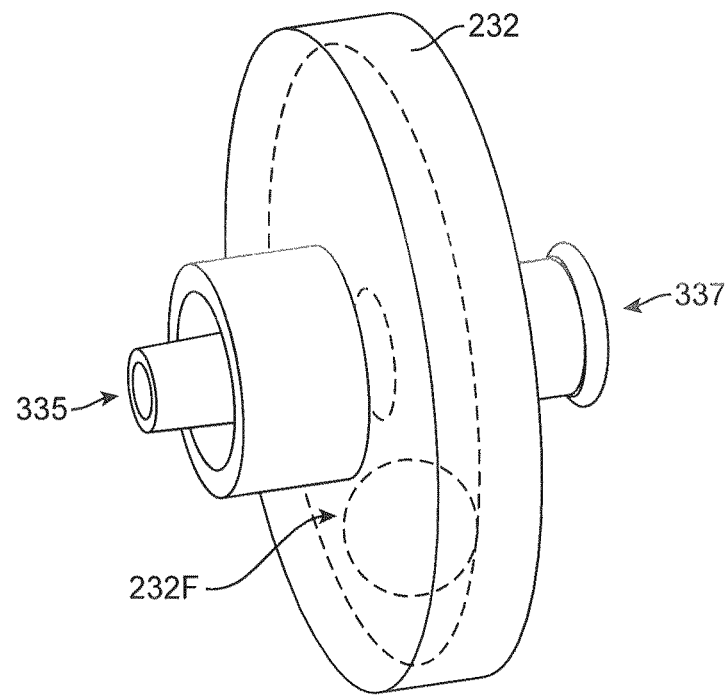

FIGS. 9A and 9B show fluid inhibiting structure comprising porous structure 232P to inhibit flow a liquid or viscous material. The fluid inhibiting structure may comprise fluid stop 232 as described herein. The fluid stop 232 comprises inlet 335 and outlet 337. As shown in FIG. 9A, the fluid stop 232 may comprise the porous structure 232P. The porous structure 232P can be located along the line 222, such that the liquid or viscous material passed through inlet 335 is deposited on the porous structure 232P. The liquid or viscous material can accumulate on the upstream side of porous structure 232P so as to inhibit flow of fluid through the porous structure. When a sufficient amount of a fluid has accumulated on the upstream side of surface of porous structure 232P, flow of fluid through the porous structure 232P is substantially decreased and in many embodiments the flow is blocked. The porous structure 232P may comprise one or more of many components commercially available from known suppliers of filters having one or more properties as described herein. As shown in FIG. 9B, the fluid stop 232 may comprise a float valve 232F. The float valve 232F can be located along the line 222, such that the liquid or viscous material passed through inlet 334 can accumulate within the fluid stop 232. When a sufficient amount of fluid has accumulated, the float valve 232F will be trigger to close to block the flow. The second fluid stop 242 may comprise similar structures to first fluid stop 232.

Figure 10:
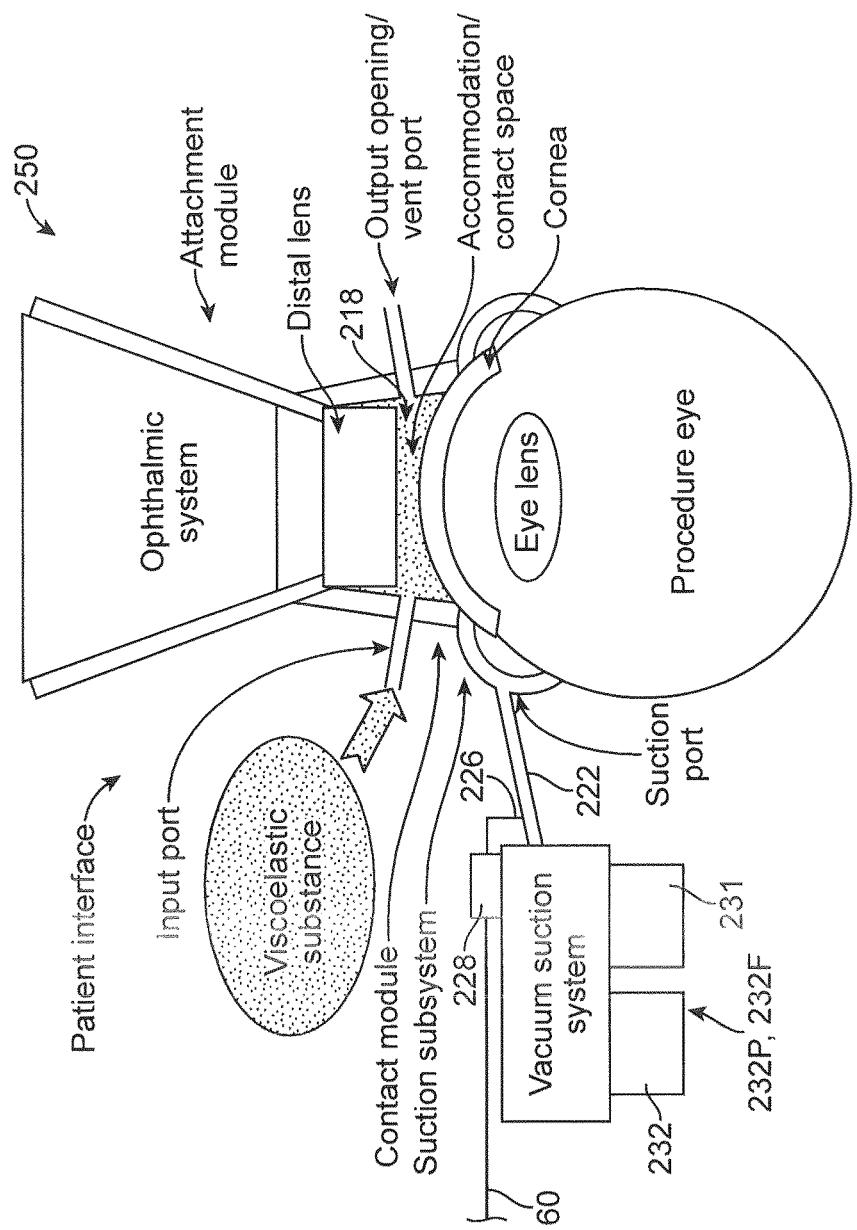
FIG. 10 shows embodiments as described herein incorporated into an adaptive patient interface.

FIG. 10 shows embodiments as described herein incorporated into an adaptive patient interface. An adaptive patient interface is described in Patent Cooperation Treaty Patent Application (hereinafter "PCT") PCT/US2011/041676, published as WO 2011/163507, entitled "ADAPTIVE PATIENT INTERFACE". The eye retention structure 250 may comprise one or more structures and functions as described herein. The container 218 can be formed on the eye. The first suction line 222 can be coupled to the suction ring placed on the eye, and the first suction line coupled to the fluid collector comprising container 231 and porous structure 232P as described herein. The coupling sensor 228 can be coupled to the suction ring and the first line 222 upstream of the porous structure 232P as described herein, for example. The coupling sensor 228 is coupled to the control electronics with communication paths 60.

Figure 11:
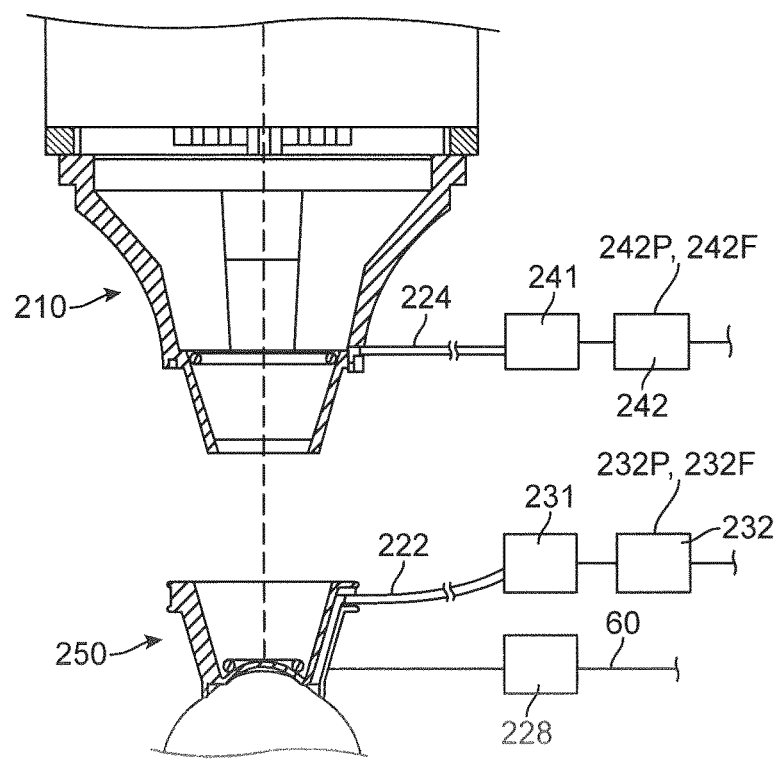
FIG. 11 shows embodiments as described herein incorporated into a device and method for aligning an eye with a surgical laser.

FIG. 11 shows embodiments as described herein incorporated into a device and method for aligning an eye with a surgical laser. A device and method for aligning an eye with a surgical laser are described in PCT/IB2006/000002, published as WO 2006/09021, entitled "DEVICE AND METHOD FOR ALIGNING AN EYE WITH A SURGICAL LASER". The eye retention structure 250 may comprise one or more structures and functions as described herein. The retention structure 250 may comprise the optically transmissive structure 212 as described herein having a concavely curved posterior surface that conforms substantially to a radius of curvature of the eye, such that the volume of the container 218 can be substantially zero when the retention ring structure is coupled to the eye. The radius of curvature of the concavely curved posterior surface example within a range from about 7 mm to about 12 mm, for example about 8.8 mm. In these embodiments, the fluid collector 231 and fluid stop 232 can be coupled to the suction line 222. The first suction line 222 can be coupled to the suction ring placed on the eye, and the first suction line coupled to the fluid collector comprising container 231 and porous structure 232P as described herein. The coupling sensor 228 can be coupled to the suction ring and the first line 222 upstream of the porous structure 232P as described herein, for example. The coupling sensor 228 is coupled to the control electronics with communication paths 60 as described herein. The second line 224 to vacuum clamp the docking structure 210 can be coupled to the fluid collector comprising container 241 and fluid stop 242 comprising porous structure 242P or float valve 242F as described herein.

Figure 12:
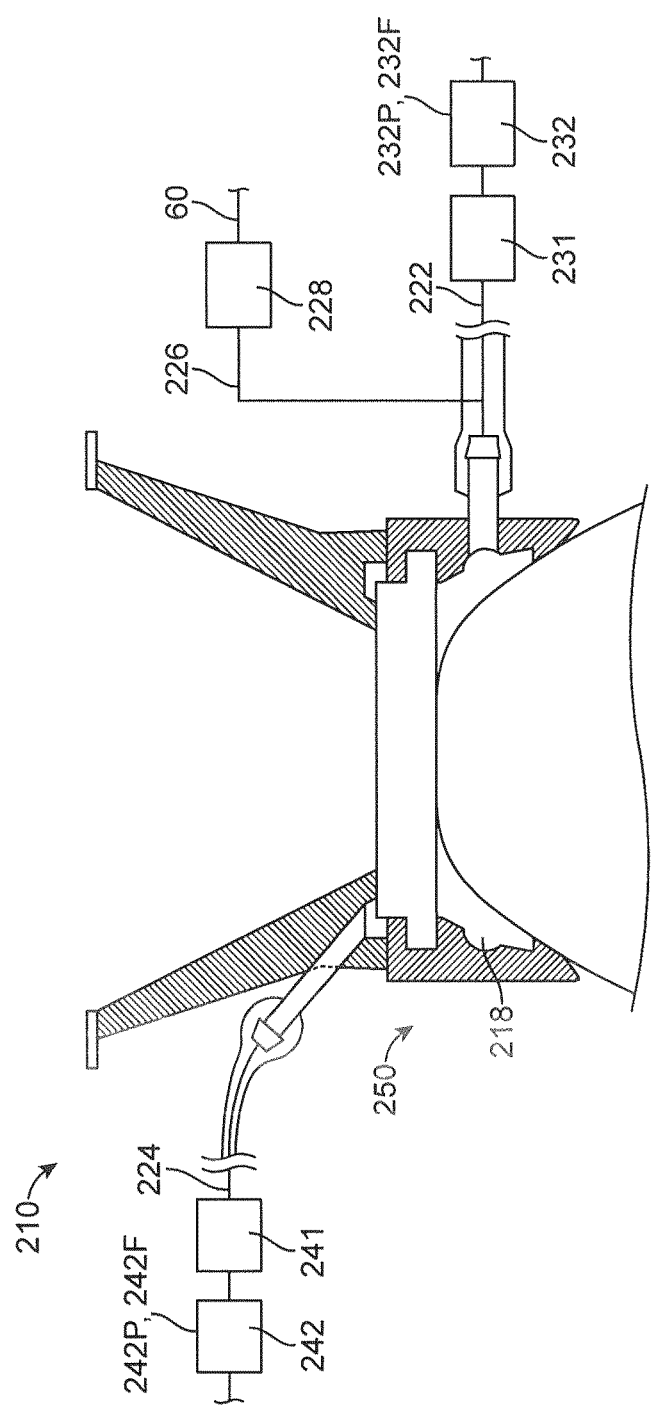
FIG. 12 shows embodiments as described herein incorporated into an apparatus for coupling an element to the eye.

FIG. 12 shows embodiments as described herein incorporated into an apparatus for coupling an element to the eye. An apparatus for coupling an element to the eye is described in U.S. application Ser. No. 12/531,217, published as U.S. Pub. No. 2010/0274228, entitled "APPARATUS FOR COUPLING AN ELEMENT TO THE EYE". The eye retention apparatus 250 can form container 218 having the volume when placed on the eye as described herein, and the optically transmissive structure 212 can be attached to retention structure 250 or docking structure 210, for example. The first line 222 can be coupled to the fluid collector comprising container 231 and fluid stop 232 comprising porous structure 232P as described herein. The coupling sensor 228 can be coupled to the suction ring and the first line 222 upstream of the porous structure 232P as described herein, for example. The coupling sensor 228 can be coupled to the control electronics with communication paths 60 as described herein. The second line 224 to vacuum clamp the docking structure 210 can be coupled to the fluid collector comprising container 241 and fluid stop 242 comprising porous structure 242P or float valve 242F as described herein.

Figure 13:
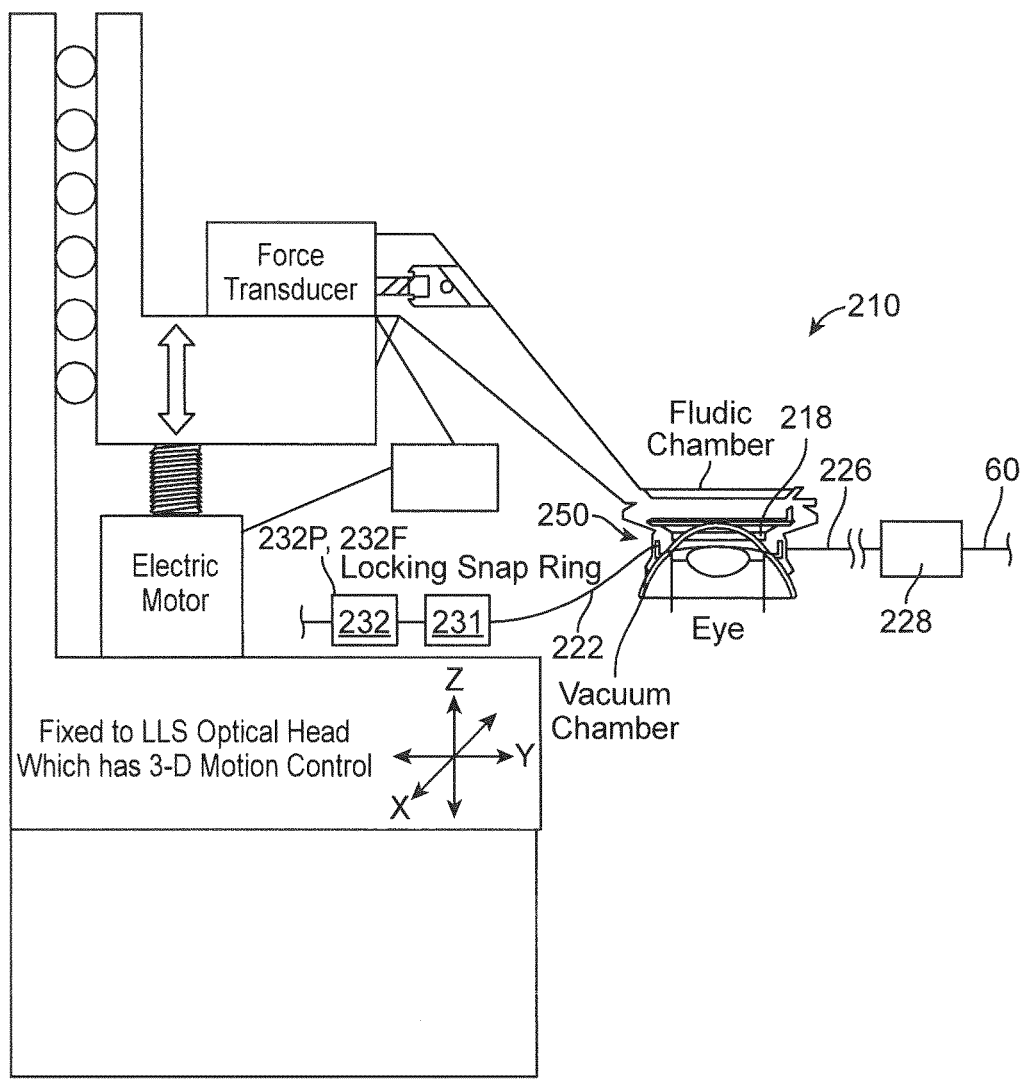
FIG. 13 shows embodiments as described herein incorporated into a servo controlled docking force device for use in ophthalmic applications.

FIG. 13 shows embodiments as described herein incorporated into a servo controlled docking force device for use in ophthalmic applications. A servo controlled docking force device for use in ophthalmic applications is described in U.S. application Ser. No. 13/016,593, published as U.S. Pub. No. US 2011/0190739, entitled "SERVO CONTROLLED DOCKING FORCE DEVICE FOR USE IN OPHTHALMIC APPLICATIONS". The eye retention apparatus 250 can form container 218 which may comprise a fluidic chamber having the volume when placed on the eye as described herein. The optically transmissive structure 212 can be attached to retention structure 250 or docking structure 210, for example. The first line 222 can be coupled to the fluid collector comprising container 231 and fluid stop 232 comprising porous structure 232P as described herein. The coupling sensor 228 can be coupled with the coupling line 226 to one or more of the suction ring or the first line 222 upstream of the porous structure 232P as described herein, for example. The coupling sensor 228 can be coupled to the control electronics with communication paths 60 as described herein.

For patient interfaces that utilize fluid as an optical medium from the laser to the cornea, as described herein, any loss of integrity of the annular suction ring inner seal may allow aspiration of fluid into the vacuum system. If, subsequent to this fluid aspiration, the seal integrity to the eye is compromised to the extent that the vacuum applied at the eye is not sufficient, the aspirated fluid needs to be cleared from the entire length of the vacuum supply tube before the instrument is able to detect the vacuum loss. Under this scenario, the latency between the vacuum detection at the end of the vacuum supply tube and the actual loss of vacuum at the eye can allow sufficient time for eye movement to cause mistreatment, or perhaps injury in the extreme case.

Accordingly, the present application contemplates an additional, separate pneumatic circuit connected directly to the suction ring to monitor the vacuum level at the eye independent of what happens in the vacuum supply line. This added circuit may be provided by the coupling sensor 228 as described above with reference to FIGS. 4 and 10-13. Further details for an exemplary embodiment of the added suction monitor are provided below.

Since fluid is not directly aspirated into the monitor pneumatic circuit after the suction ring loses its seal, a latency inherent in monitoring the vacuum supply circuit as described above is avoided. One detail in utilizing this approach worth mentioning is that the vacuum monitor circuit itself (e.g., pressure transducer 228 in FIG. 4) may aspirate a small about of fluid after repeated suction ring seal breaks. This does not significantly influence the vacuum loss response time, but may lower the absolute value of the monitor measurement erroneously indicating a vacuum loss. Accordingly, a valve may be added at the end of the monitor line which will cycle on and off, meaning it will open to atmosphere briefly then close, to clear fluid from the monitor circuit until the expected vacuum level is reached. A specific example is described below.

Figure 14:
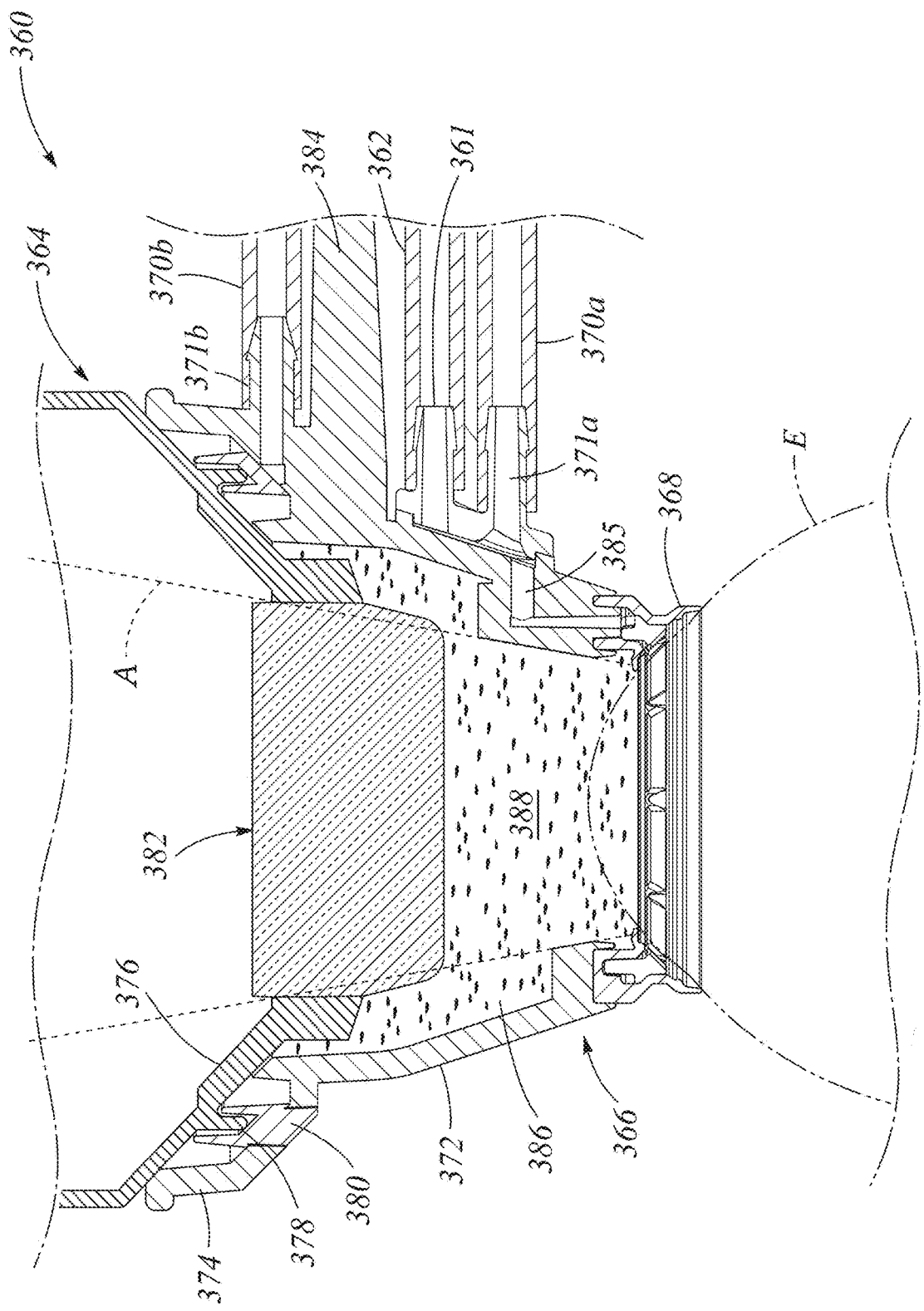
FIG. 14 is a vertical section view through an exemplary patient interface that uses liquid as an optically transmissive medium in contact with an eye, showing a preferred monitoring port for a suction ring thereof.

FIG. 14 is a vertical section view through an exemplary patient interface 360 that uses liquid as an optically transmissive medium in contact with an eye, illustrating a suction monitoring circuit port 361 and attached conduit 362. In this embodiment, the patient interface 360 comprises a two-part assembly with an upper or docking member 364 having features (not shown) configured to be removably coupled to a diagnostic and interventional unit, such as that described above in reference to system 2 shown in FIG. 1. The upper member 364 removably couples to a lower eye-contacting member 366 via suction, as will be described below and in a similar manner as the interface between docking structure 210 and eye retention structure 250 shown in FIG. 4.

The exemplary patient interface 360 incorporates a compliant suction ring 368 at a lower end of the eye-contacting member 366 for coupling with the eye E, for example, using vacuum. More specifically, at the bottom end of a frusto-conical body 372, the elastomeric suction ring 368 defines a pair of annular compliant walls or blades (not numbered) that define a space therebetween. A lower fluid conduit 370a attaches to a corresponding port 371a having a lumen that is in fluid communication through channels in the patient interface with the space between the blades. The fluid conduit 370a extends from the suction ring 368 to and through a series of components including a vacuum supply source, as will be described with reference to FIG. 15. As such, the first fluid conduit 370a is the vacuum supply conduit. To couple the patient interface 360 to the generally spherical surface of the eye E, the lower or distal end thereof is placed in contact with the cornea of the eye E and suction drawn through the vacuum supply conduit 370a to the suction ring 368.

The eye-contacting member 366 of the patient interface 360 in this embodiment comprises a generally frustoconical body 372 having an upper cylindrical rim 374 within which upper member 364 mounts. The upper member 364 includes a generally frustoconical wall 376 having a small circular flange 378 projecting downward therefrom that fits within an annular space defined within the two walls or blades of an elastomeric seal 380. This helps center the two components. Vacuum communicated through an upper fluid conduit 370b leading to a port 371b pulls the frustoconical wall 376 against the blades of the elastomeric seal 380, thus securing the upper member 364 to the eye-contacting member 366.

The rigid, preferably molded, body 372 of the eye-contacting member 366 has a generally annular cross-section and defines therein a throughbore. Likewise, the wall 376 of the upper member 364 defines a throughbore. An optical lens 382 mounts within the patient interface 360; and in the illustrated embodiment mounts across the throughbore of the upper member 364 so as to be positioned above the throughbore defined by the suction ring 368. Because of the gradually narrowing walls of the components of the patient interface 360, a frusto-conical optical field of view A (shown in dashed line) is defined by the patient interface through the optical lens 382 and to the eye E. The diagnostic and interventional unit described above can see and act on the eye E directly through the field of view A by virtue of the transparent lens 382.

In a preferred embodiment, a small radially-projecting handle 384 permits a physician or technician to easily manipulate the eye-contacting member 366. The trio of ports 361, 371a, 371b and corresponding fluid conduits 362, 370a, 370b extend radially away in the same direction as the handle 384, and are thus nominally braced when held with the handle when a user manipulates the lower member 366, which has a relatively low mass. Note the vacuum supply conduit 370a and the suction monitoring circuit conduit 362 share a pneumatic channel 385 leading from the suction ring 368, then split with the supply on the bottom and the monitor on the top. This arrangement guides aspirated fluid to preferentially flow by intertia and gravity into the supply circuit as opposed the monitoring circuit.

In an exemplary procedure, a patient support chair or bed 34 (FIG. 1) is rotated out from under the diagnostic and interventional unit (e.g., system 2) to a suction ring capture position. A physician or technician can then easily engage the eye-contacting member 366 of the interface 360 to the patient's eyes E using the suction ring 368. The operator then rotates the support bed 34 to the patient treatment position under the diagnostic and interventional unit, and the eye-contacting member 366 and upper member 364 are coupled together, into the configuration shown in FIG. 14. The optical lens 382 is thus held securely centered within the patient interface 360, and above the eye E, readying the system for a laser-assisted ophthalmic procedure.

A suitable liquid 386 (e.g., a sterile buffered saline solution (BSS)) is then introduced to the patient interface 360 (preferably through open apertures, not shown) so as to settle by gravity into a fluid chamber 388 therein, filling the chamber and rising into contact with the optical lens 32. Alternatively, the liquid 386 may be introduced into the chamber 386 above the eye E prior to coupling the upper member 364 to the lower member 366. The fluid chamber 388 includes at least that portion of the throughbore in the patient interface 360 within the eye-contacting member 366, below the lens 382, and within the conical field of view A. The posterior (lower) surface of the optical lens 382 is thus spaced vertically from the anterior (upper) surface of the patient's cornea across a region of the suitable liquid 386, which acts as an optically transmissive medium. Although not shown, inlet and outlet ports to the chamber 388 are provided in the eye-contacting member 366 for supplying and draining liquid as needed, in particular for maintaining a pressure equilibrium.

Figure 15:
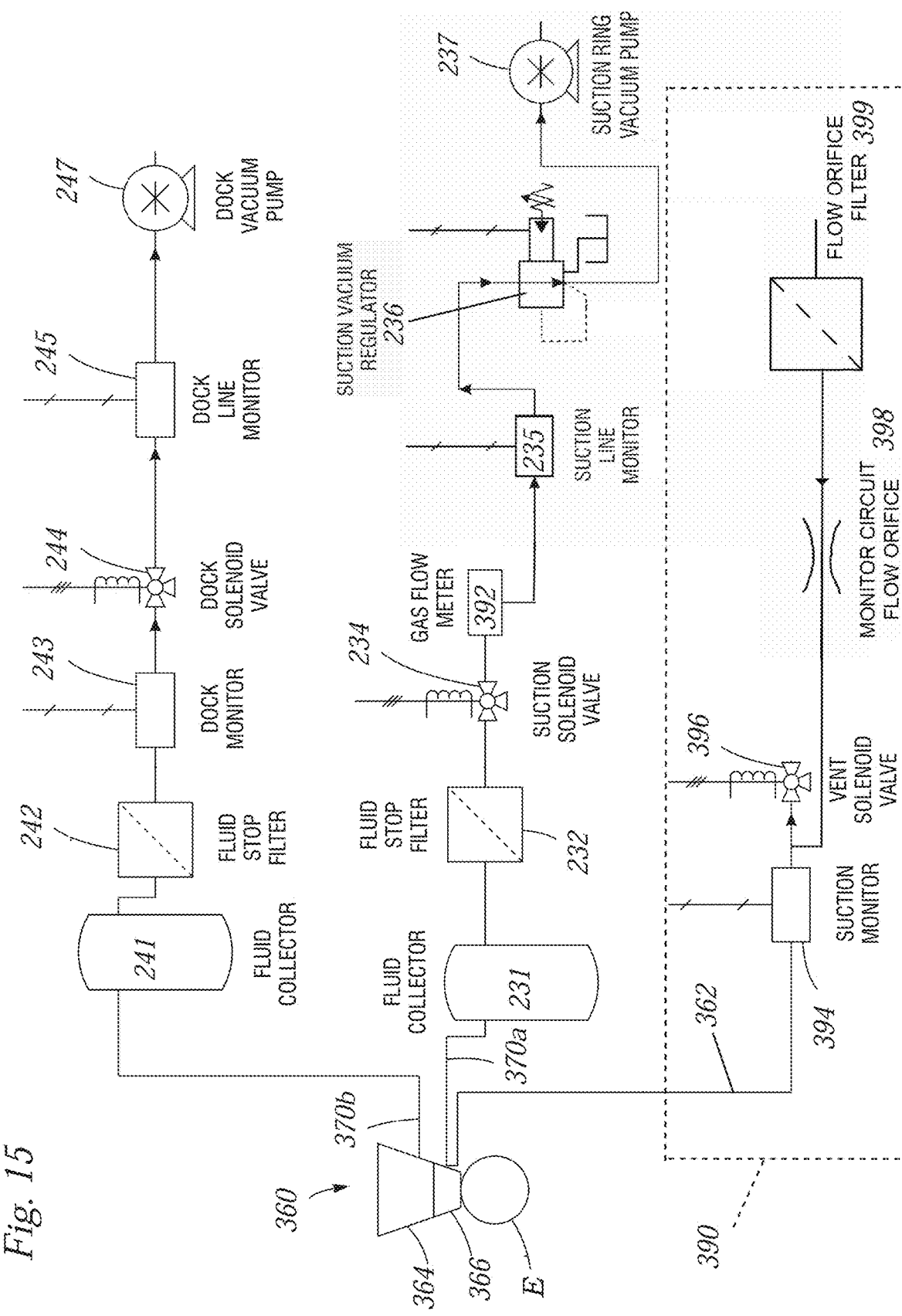
FIG. 15 is a schematic circuit diagram of various support systems connected to the exemplary patient interface of FIG. 14 illustrating a suction monitoring line.

FIG. 15 is a schematic circuit diagram of various support systems connected to the exemplary patient interface of FIG. 14 illustrating a suction monitoring line. FIG. 15 is much like the diagram of FIG. 4, with greater detail shown of the suction monitoring circuit, indicated in dashed outline 390, which replaces the coupling monitor 228. Aside from the patient interface numbering, elements of the rest of the circuit diagram will be labeled with the same numbering as was presented in FIG. 4, and will not be further described. In particular, components 241-247 along the upper fluid conduit 370b leading from the patient interface 360 supply and control suction to the coupling interface between the two components 364, 366 of the patient interface. Likewise, components 231-237 along the second suction line or conduit 370a supply and control suction to the suction ring 368. An additional gas flow meter 392 in series between the suction solenoid valve 232 and the vacuum regulator 236 may be provided to indirectly sense liquid loss. The flow meter 392, which may be a gas flow meter, monitors gas flow within the first suction conduit 370a, and provides an alternative method for detecting major suction loss as well as slow leaks by utilizing a sensor of high sensitivity. It should be understood that though the control electronics 54 and electronic communication paths 60 are not shown in FIG. 15, they are implicitly present and may take the form as shown in FIG. 4.

The suction monitoring circuit 390 comprises the suction monitoring conduit 362, a suction sensor or monitor 394, and a vent solenoid valve 396. As explained above, the conduit 362 shares a pneumatic channel 385 (FIG. 14) with the supply conduit 370a, but has a much smaller overall volume and thus a more sensitive pressure reading is available. This enables a faster detection of loss of vacuum. Desirably, the total volume of the suction monitoring circuit 390 is between about 1-10% of the volume in the vacuum supply line 370a.

Because of its port position above the supply conduit (see port 362 in FIG. 14), the monitoring conduit 362 is less prone to aspiration of liquid from the patient interface 360. However, some liquid or condensation may accumulate within the conduit 362, at which point the vent solenoid valve 396 may be actuated to clear the fluid in the line. The indication for fluid aspiration into the monitor circuit 362 is that a full vacuum cannot be attained as indicated by the suction monitor 394. The control electronics will cycle ON the vent solenoid valve 396 for short time periods until full vacuum is reached.

Fluid is not directly aspirated into the monitor pneumatic circuit 390 after the suction ring 368 loses its seal, and thus the latency inherent in monitoring the vacuum supply circuit 370a is avoided. However, the vacuum monitoring circuit 390 can aspirate a small amount of fluid under certain circumstances, such as repeated suction breaks and re-application to the eye. Fluid in the monitoring line 362 can slow the response of the detection circuit potentially reducing the benefits of the fast response to vacuum loss. As described previously, the monitoring line vent solenoid valve 396 could be actively controlled to actuate in a manner to assure that the sense line 360 is clear of fluid. However, due to the limited amount of information from the instrument sensors, solenoid valve 396 may be insufficient.

Alternatively or in addition, a controlled leak, either through the solenoid valve 396 or through a separate flow orifice 398, may be incorporated into the suction monitoring conduit 362 so that any substantial fluid that enters the conduit will travel back toward the patient interface 360 by virtue of the vacuum into the vacuum supply conduit 370a. The flow orifice 398 connects to the suction monitoring conduit 362 upstream of the vent solenoid valve 396. To prevent contamination of the system, a flow orifice filter 399 would also be provided. In place of actively cycling the vent solenoid valve 396, a controlled passive vent provided by the flow orifice 398 continuously evacuates any aspirated fluid. That is, there is a constant negative pressure differential toward the patient interface 360 which moves fluid in that direction. A simple flow orifice should be sized large enough to provide adequate flow to clear fluid in an appropriately short amount of time. Stated another way, the magnitude of the controlled leak should be sufficient to create an airflow or $\Delta P$ toward the patient interface 360 which overcomes the frictional forces holding fluid to the inner walls of the conduit 362. At the same time, the flow orifice 398 should be small enough to avoid increasing the time to attain full vacuum to an unacceptable level.

An important additional benefit of the controlled leak approach is that pinching off of the vacuum tubes between the patient and the instrument will be immediately detected. Pinching the vacuum circuit tube 370a will stop the vacuum supply to the monitor line 362 which will allow the passive vent 398 to decay the vacuum contained in the monitor line to the point where the pressure differential between the suction supply sensor and the suction monitor sensor will trigger an error condition.

As mentioned above, the control electronics 54 receive input from the suction monitor 394 either wirelessly or through the communication paths 60. The suction monitor sensor output is monitored and evaluated by the system level software to create an error indication if a vacuum loss event is detected during the laser treatment. The suction monitor 394 and vent solenoid valve 396 are under local hardware control, though they could be under system level software control.

Figure 16:
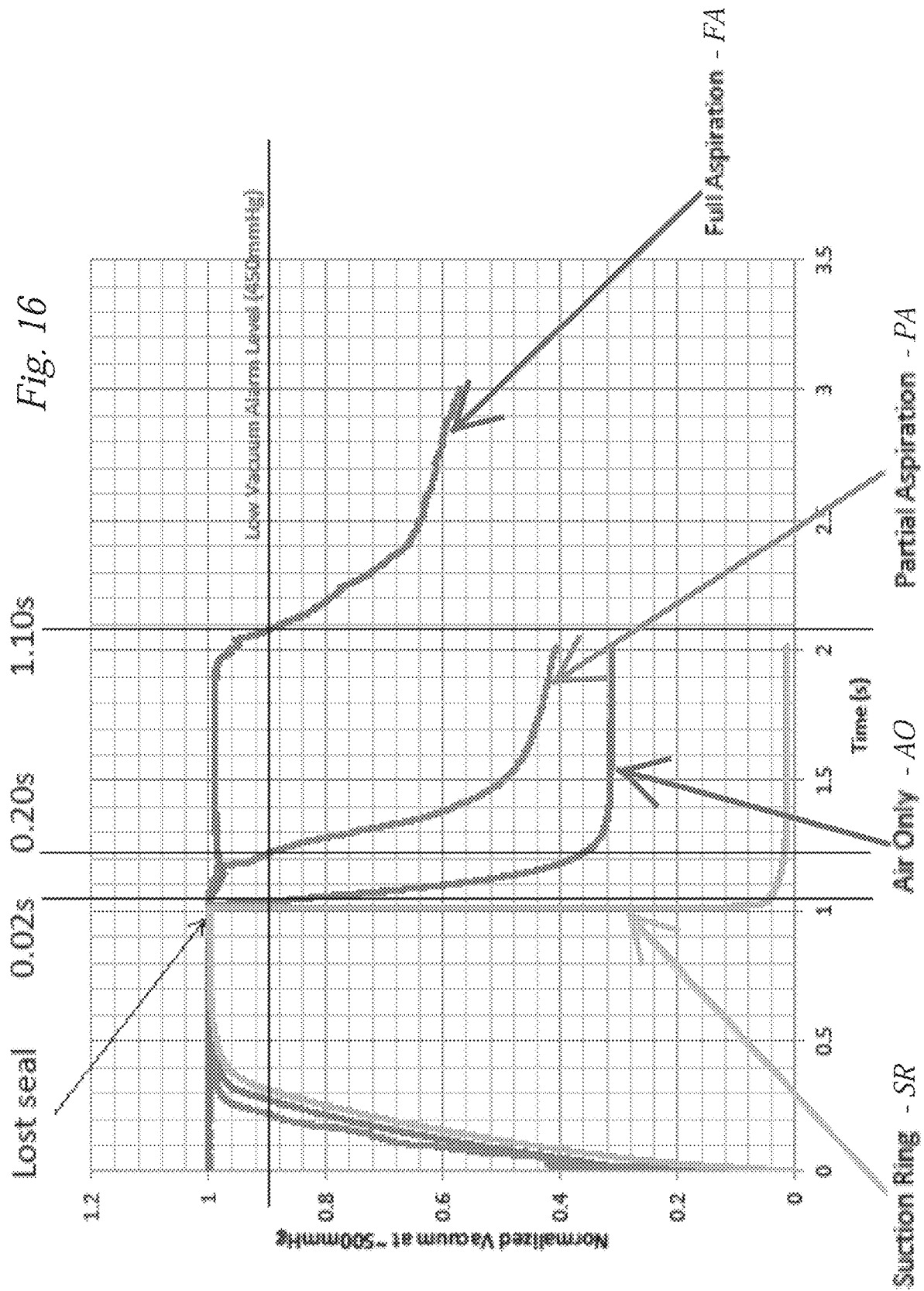
FIG. 16 is a graph depicting the relative suction loss detection performance benefit of the suction monitor circuit versus the response of a suction supply line monitor with different levels of aspiration.

FIG. 16 is a graph depicting the relative suction loss detection performance of the suction monitor circuit 390 versus the response of a suction supply line monitor with different levels of aspiration. The graph shows four pressure curves from measurements taken using an actual patient interface 360 and the corresponding suction and monitoring circuits. An operating vacuum magnitude of 500 mm Hg is used to secure the suction ring 368 to an eye of a patient (or prosthetic test eye). The test begins at 0 seconds and at precisely 1 second the seal between the suction ring 368 and the eye is artificially and instantly broken, thus leading to a loss of vacuum in the system. All four pressure curves respond to this loss of vacuum by producing different changes in air pressure readings. Per convention, an alarm will sound if the vacuum level drops below 10% of its operating magnitude, or to 450 mm Hg.

Upon suction loss the monitor circuit 390, which essentially measures the pressure within the suction ring (SR), drops to the alarm level almost immediately, within 10 s of milliseconds. The supply circuit monitor in a vacuum supply conduit 370a with air only (AO), or no aspirated fluid, in the tubing responds slightly slower. With a small amount of fluid in the vacuum supply tubing 370a, or when partially aspirated (PA), the response slows to 100s of milliseconds. Finally, when the vacuum supply tubing 370a is full of fluid, or fully aspirated (FA), response slows to on the order of a second. Thus, the provision of the suction monitoring circuit 390 provides an important redundancy for the monitor within the supply line which may become filled with fluid for a reduced response time. Furthermore, the supply line has a much greater volume than the monitoring circuit such that a greater amount of fluid can accumulate therein before the response time deteriorates, at which point it may increase response time to exceed safety requirements when the laser is in an operating mode.

FIG. 17 shows a method 400 of treating a patient with the eye retention apparatus.

The method 300 may use one or more of the structures as described herein, and one or more functions of the one or more structures may be used to perform the method 400 as described herein.

At a step 405, a fluid collector having a volume is provided with a porous structure.

At a step 410, suction is provided to a suction line coupled to the fluid collector and the porous structure as described herein.

At a step 415, the patient is placed on a support.

At a step, 420 a speculum is placed in the eye.

At a step 425, the retention structure with the suction ring is placed on the eye to define container.

At a step 430, the eye is aligned with the retention structure.

At a step 435, coupling suction is applied to the eye.

At a step 440, eye coupling is measured with suction upstream of the porous structure as described herein.

At a step 445, suction is measured downstream of porous structure as described herein.

At a step 450, provide an indication to the user when the eye retention structure is held to eye with suction based on coupling suction.

At a step 455, a liquid or viscous solution is applied to container on eye.

At a step 460—at least partial blockage of porous structure is identified when coupling suction above a threshold and downstream suction below a second threshold At a step 465, the above steps are repeated until the eye is coupled to the retention structure with suction.

At a step 470, the docking structure is coupled to the retention structure with axial movement.

At a step 475, suction is a applied to gap between retention structure and docking structure to clamp retention structure to docking structure with suction.

At a step 480, eye coupling suction is measured.

At a step 485, alignment of eye with retention structure is determined.

At a step 490, the eye is at least partially treated with the laser.

At a step 495, coupling suction is measured.

At a step 500, a warning is provided to the user when eye coupling suction rises above a warning threshold.

At a step 505, laser firing is interrupted when eye the measured coupling suction is above an interruption threshold pressure.

At a step 510, an indicator is provided to the user when the measured coupling pressure is above the threshold pressure.

At a step 515, the eye is re-aligned with the retention structure.

At a step 520, the eye is re-coupled to the eye retention structure.

At a step 525, the laser treatment is resumed.

At a step 530, the laser treatment has been completed.

At a step 535, the eye is decoupled from the retention structure.

At a step 540, the retention structure is decoupled from docking structure

At a step 545, the remaining portion of the eye surgery is completed, for example with removal of the lens and insertion of an IOL.

Although the above steps show method 400 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 400 may be performed with the circuitry as described herein, for example one or more of the processor or logic circuitry such as the programmable array logic for field programmable gate array. The circuitry may be programmed to provide one or more of the steps of method 400, and the program may comprise program instructions stored on a computer readable memory or programmed steps of the logic circuitry such as the programmable array logic or the field programmable gate array, for example.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. An apparatus to treat an eye, the apparatus comprising:
a patient interface comprising an annular suction ring to engage an anterior surface of the eye, the suction ring comprising an opening to receive a portion of the eye and a channel to couple to the eye with suction, the patient interface defining a fluid volume over the eye adapted to contain a quantity of fluid to act as an optical transmissive medium when the suction ring is coupled to the eye;

a suction conduit in fluid communication with the suction ring to couple a suction source to the eye;

a supply conduit pressure sensor in the suction conduit to monitor pressure therein;

a monitoring circuit including a monitoring conduit in fluid communication with the suction ring and a monitoring pressure sensor to monitor pressure in the monitoring conduit, the monitoring conduit having a substantially smaller volume than the suction conduit; and a processor coupled to the monitoring pressure sensor, the processor comprising instructions to interrupt firing of a laser when the pressure measured with the monitoring pressure sensor rises above a threshold amount.

2. The system of claim 1, wherein the monitoring circuit has a volume that is between about 1-10% of the volume in the suction conduit.

3. The system of claim 1, wherein the monitoring circuit further comprises a suction monitor and a vent solenoid valve, and the processor activates the vent solenoid valve when the suction monitor senses a suction loss within the monitoring circuit.

4. The system of claim 3, wherein the monitoring circuit further comprises a passive vent orifice open to an atmosphere via a filter, the vent orifice maintaining a small flow of air through the monitoring conduit to reduce an amount of liquid in the monitoring conduit.

5. The system of claim 1, wherein the monitoring circuit further comprises a passive vent orifice open to an atmosphere via a filter, the vent orifice maintaining a small flow of air through the monitoring conduit to reduce an amount of liquid in the monitoring conduit.

6. The system of claim 1, wherein the suction conduit communicates with a suction port extending outward from the patient interface, and the monitoring conduit communicates with a monitoring port extending outward from the patient interface, wherein the suction port and the monitoring port communicate with a common channel within the patient interface in communication with the suction ring.

7. The system of claim 6, wherein the patient interface comprises a lower portion having the suction ring on a lower end, and wherein the suction port is located below the monitoring port, and both ports are located above the level of the suction ring.

8. The system of claim 6, wherein the patient interface comprises a lower portion having the suction ring on a lower end, and an upper portion that mates with the lower portion and has an optical lens therein, wherein when the upper portion mates with the lower portion and liquid is introduced to the interface container volume, the liquid rises to contact the optical lens.

9. The system of claim 8, wherein the patient interface includes a second suction port leading to a second seal on an upper end of the lower portion, the upper portion and lower portion mating by communicating suction to the second seal.

10. The system of claim 9, further including a second suction conduit connected to the second suction port, the second suction conduit leading to a second suction circuit, and a second supply conduit pressure sensor in the second suction conduit to monitor a supply suction pressure within the second suction conduit, wherein the processor is coupled to the second supply conduit pressure sensor and further comprises instructions to interrupt the ophthalmic procedure when the supply suction pressure in the second suction conduit rises above a threshold amount.

* * * * *